(12) United States Patent
Geist et al.

(10) Patent No.: US 8,366,715 B2
(45) Date of Patent: Feb. 5, 2013

(54) MAGNETIC TARGETING SYSTEM FOR FACILITATING NAVIGATION

(75) Inventors: Wyatt Drake Geist, Davie, FL (US); Christopher Walsh, Parkland, FL (US)

(73) Assignee: Magrod, LLC, Davis, FL (US)

( * ) Notice: Subject to any disclaimer, the term of this patent is extended or adjusted under 35 U.S.C. 154(b) by 62 days.

(21) Appl. No.: 13/151,756

(22) Filed: Jun. 2, 2011

(65) Prior Publication Data

US 2011/0238117 A1 Sep. 29, 2011

Related U.S. Application Data

(63) Continuation of application No. 12/157,397, filed on Jun. 10, 2008, now Pat. No. 7,976,546, which is a continuation-in-part of application No. 11/462,592, filed on Aug. 4, 2006, now Pat. No. 8,092,458.

(51) Int. Cl.
- A61B 17/58 (2006.01)
- A61B 17/60 (2006.01)
- A61B 17/70 (2006.01)
- A61F 2/00 (2006.01)

(52) U.S. Cl. .................................. 606/86 A; 606/99

(58) Field of Classification Search ............. 606/86 A, 606/86 B, 86 R, 99, 914–916, 246
See application file for complete search history.

(56) References Cited

U.S. PATENT DOCUMENTS

| | | | |
|---|---|---|---|
| 5,049,151 A | 9/1991 | Durham et al. |
| 5,127,913 A | 7/1992 | Thomas, Jr. |
| 5,514,145 A | 5/1996 | Durham et al. |
| 5,797,911 A | 8/1998 | Sherman et al. |
| 5,851,183 A | 12/1998 | Bucholz |
| 6,074,394 A | 6/2000 | Krause |
| 6,086,596 A | 7/2000 | Durham |
| 6,127,597 A | 10/2000 | Beyar et al. |
| 6,162,228 A | 12/2000 | Durham |
| 6,168,595 B1 | 1/2001 | Durham et al. |
| 6,226,548 B1 | 5/2001 | Foley et al. |
| 6,236,875 B1 | 5/2001 | Bucholz et al. |
| 6,503,249 B1 | 1/2003 | Krause |
| 7,011,660 B2 | 3/2006 | Sherman et al. |
| 7,835,778 B2 | 11/2010 | Foley et al. |
| 7,976,546 B2 | 7/2011 | Geist et al. |
| 8,092,458 B2 | 1/2012 | Geist et al. |
| 8,092,460 B2 | 1/2012 | Geist et al. |
| 8,092,461 B2 | 1/2012 | Geist et al. |
| 2003/0065373 A1 | 4/2003 | Lovett et al. |
| 2005/0055089 A1 | 3/2005 | Macoviak et al. |
| 2005/0075562 A1 | 4/2005 | Szakelyhidi, Jr. et al. |
| 2005/0085714 A1 | 4/2005 | Foley et al. |
| 2005/0277934 A1 | 12/2005 | Vardiman |
| 2006/0079894 A1 | 4/2006 | Colleran et al. |
| 2006/0149135 A1 | 7/2006 | Paz |

(Continued)

FOREIGN PATENT DOCUMENTS

| | | |
|---|---|---|
| WO | WO 2009105104 | 8/2009 |
| WO | WO 2009152243 | 12/2009 |

*Primary Examiner* — Sameh Boles
(74) *Attorney, Agent, or Firm* — Mchale & Slavin, P.A.

(57) ABSTRACT

The present invention describes a magnetic targeting system suitable for guiding a biocompatible device to a target area within the body (in vivo) and method of using the same. The system includes a targeting member having a steering material and is attached to the biocompatible device. The system also includes at least one anchoring member constructed and arranged for the inclusion of a magnetic material effective for influencing the traversal of the steering material, in vivo. The magnetic material is configured and sized so as to positionable external of the anchoring member, in vivo. The magnetically influenced anchoring member interacts with the targeting member such that the biocompatible device is positionable relative to the target area. An extender and connector have threads indexed to a securing set screw to facilitate positioning and affixation of the biocompatible material.

7 Claims, 49 Drawing Sheets

U.S. PATENT DOCUMENTS

| | | |
|---|---|---|
| 2007/0191836 A1 | 8/2007 | Justis |
| 2007/0191845 A1 | 8/2007 | Justis et al. |
| 2007/0213714 A1 | 9/2007 | Justis |
| 2008/0039845 A1 | 2/2008 | Bonutti et al. |
| 2008/0140100 A1 | 6/2008 | Gertner |
| 2008/0312704 A1* | 12/2008 | Hestad et al. ............... 606/86 A |
| 2009/0287255 A1 | 11/2009 | Erickson et al. |

* cited by examiner

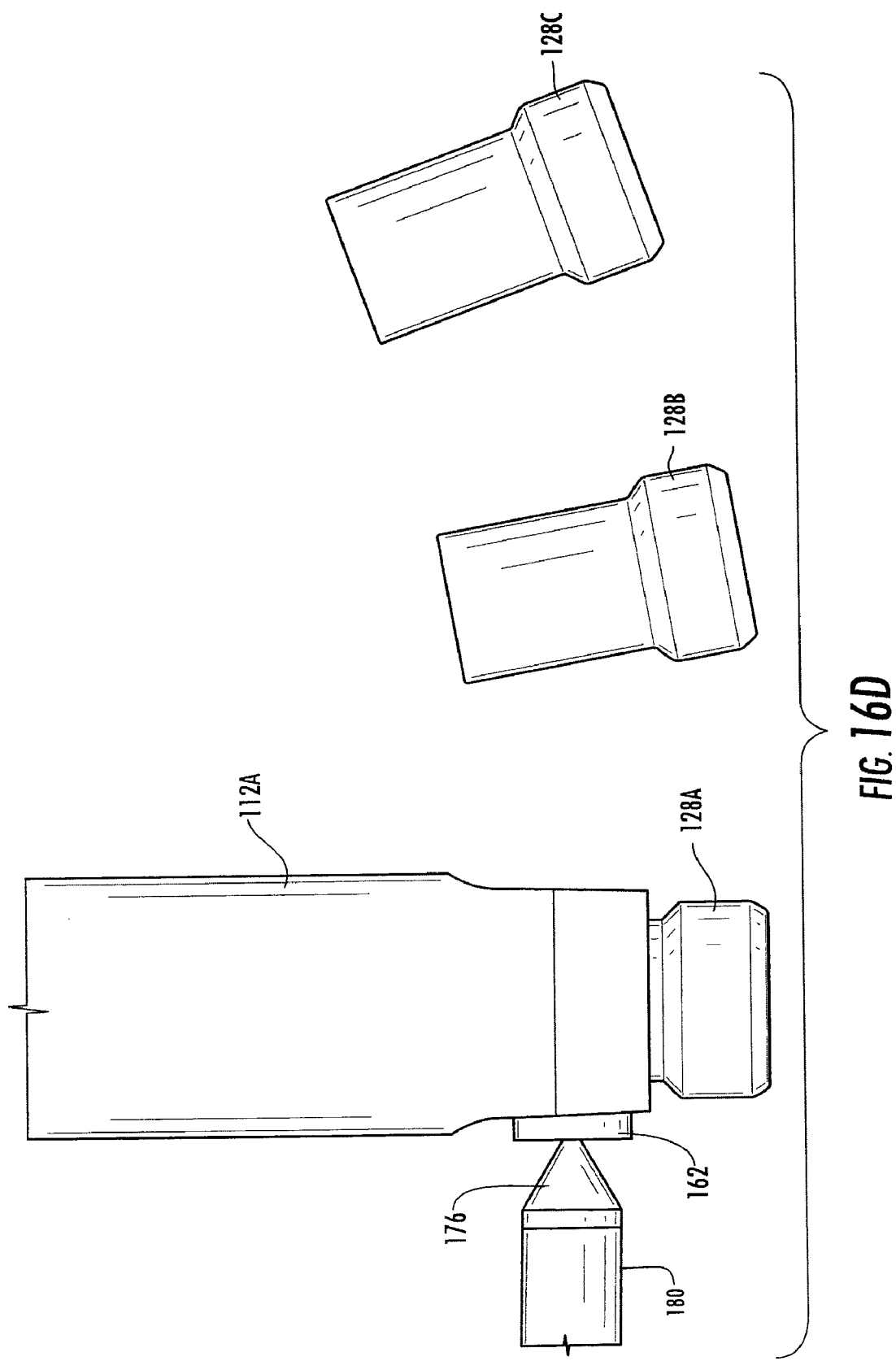

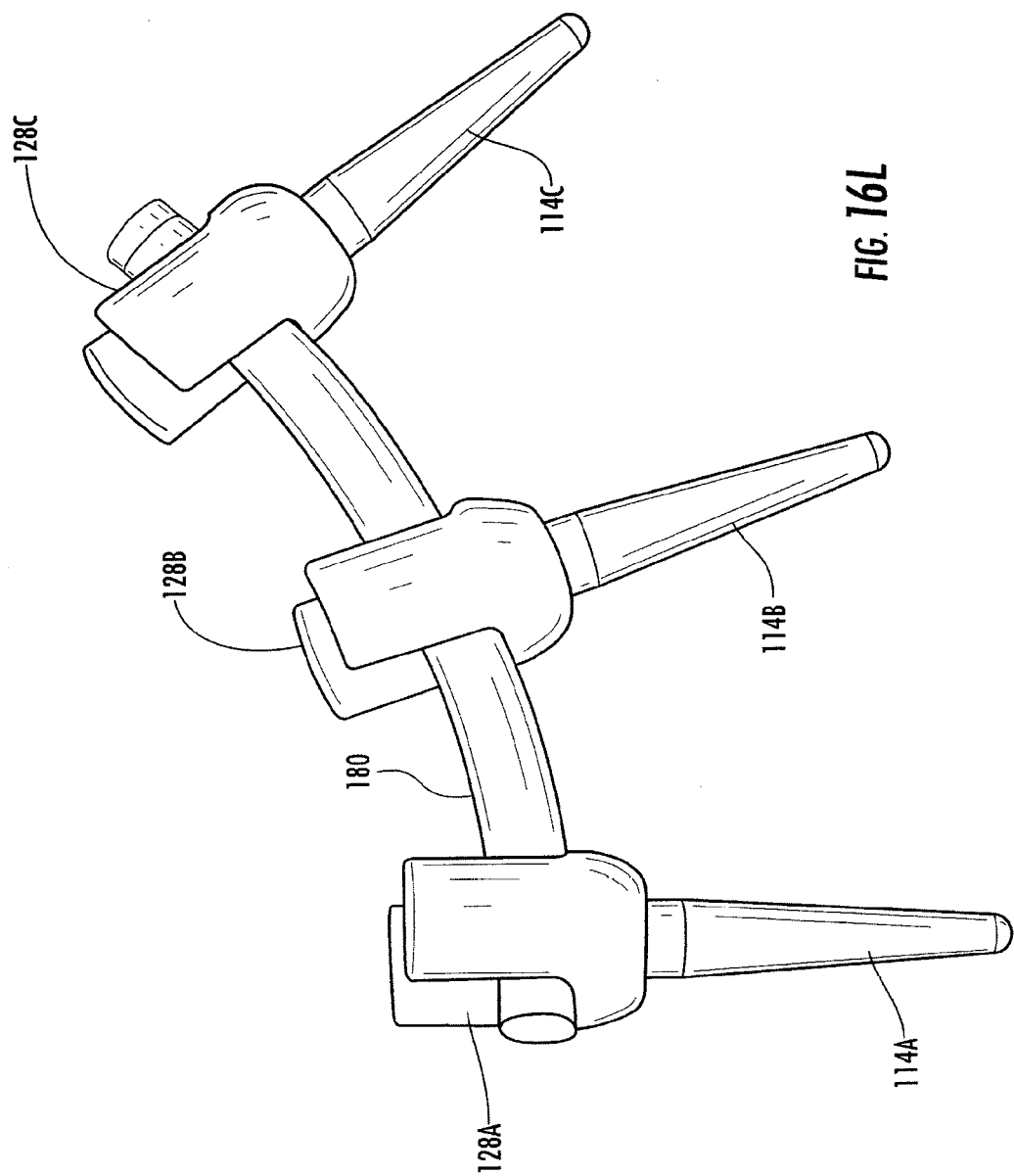

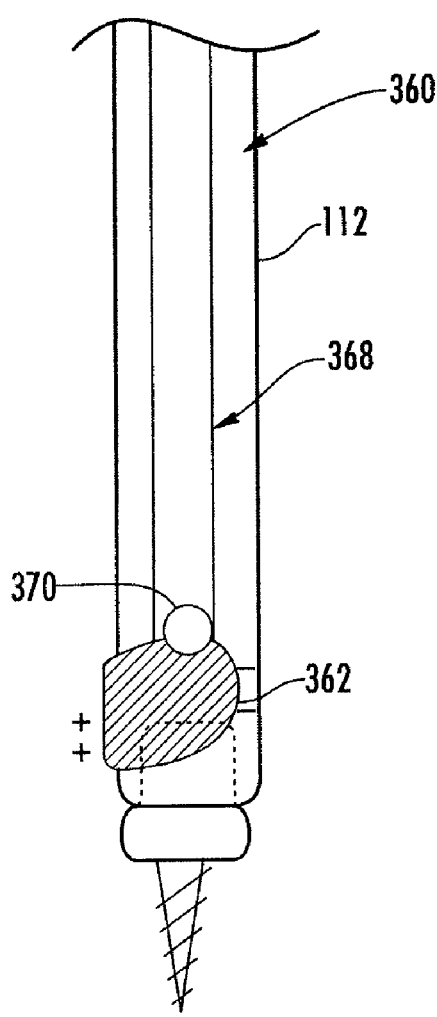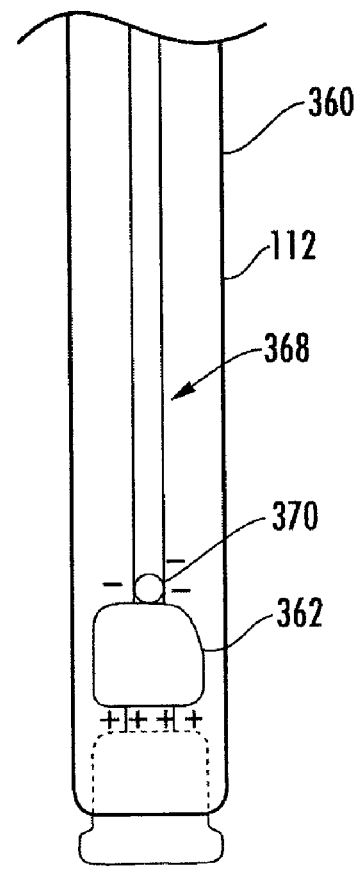
FIG. 18B
FIG. 18C

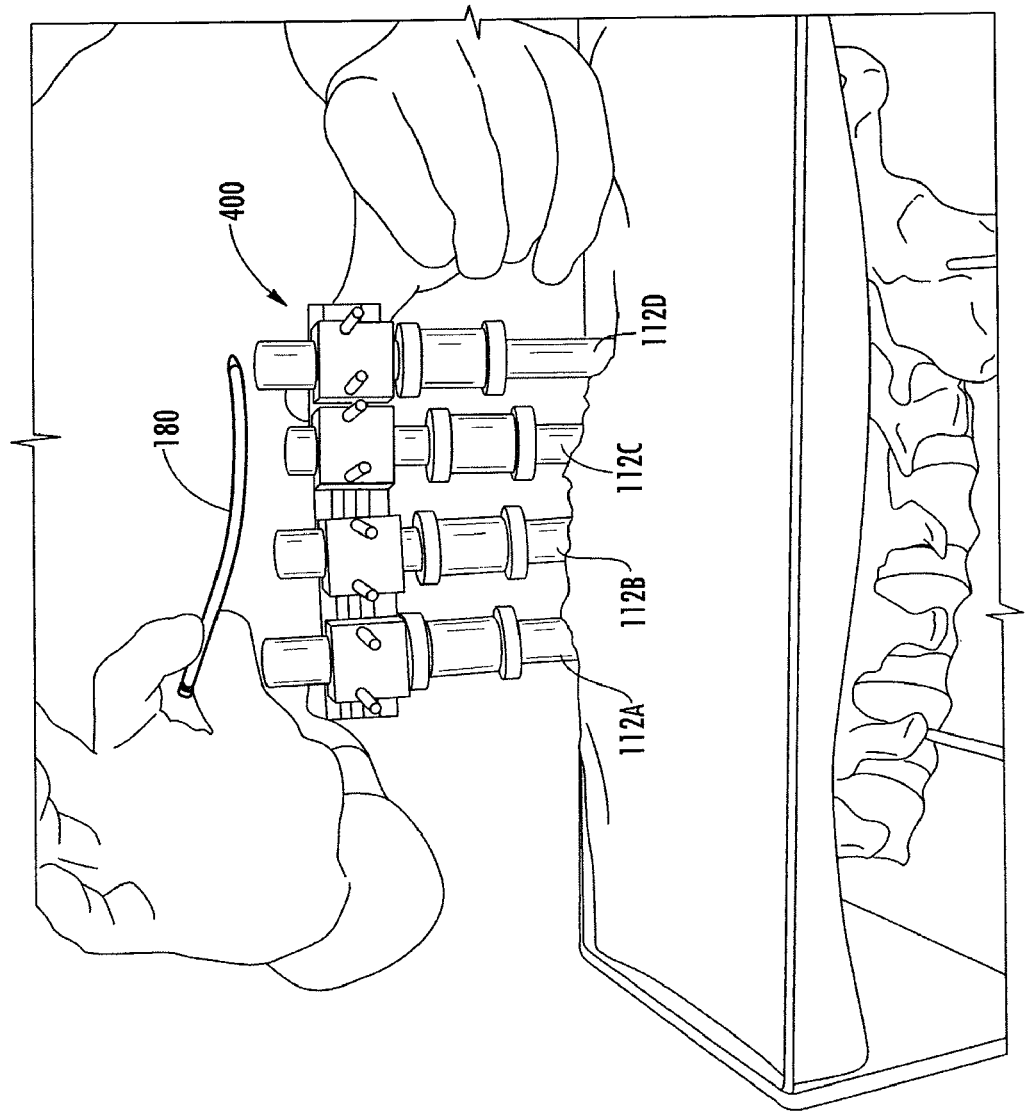

MAGNETIC TARGETING SYSTEM FOR FACILITATING NAVIGATION

CROSS REFERENCE TO RELATED APPLICATIONS

This application is a continuation of U.S. patent application Ser. No. 12/157,397, filed on Jun. 10, 2008 now U.S. Pat. No. 7,976,546, entitled "MAGNETIC TARGETING SYSTEM FOR FACILITATING NAVIGATION," which is a continuation-in-part of U.S. patent application Ser. No. 11/462,592, filed on Aug. 4, 2006 now U.S. Pat. No. 8,092,458, entitled "MAGNETIC TARGETING SYSTEM AND METHOD OF USING THE SAME," which are hereby incorporated herein by reference.

FIELD OF THE INVENTION

The invention generally relates to surgical implants; particularly to a system and method for stabilization of adjacent bony structures; most particularly to a system to help navigate an interconnecting means between multiple bony stabilization devices.

BACKGROUND OF THE INVENTION

It is widely held that healing and/or structural correction is greatly facilitated when a bone is stabilized in the proper position. Various devices for stabilization of bone are well known and routinely practiced in the medical arts. For example, an abnormal spine can be stabilized using a substantially rigid or semi-rigid interconnecting means (rod or plate) and fastening means (screws, clamps, hooks, claws, anchors, or bolts). Multiple fasteners are placed into the spinal pedicle of each vertebra and linked by at least one interconnecting means. One of the more difficult aspects is the surgical insertion of the interconnecting means along a fixed path of delivery longitudinally along the vertebrae and through each of the multiple fastening means between multiple vertebrae. Once in place, this system substantially immobilizes the spine and promotes bony fusion (arthrodesis).

Traditionally, the surgical techniques for stabilization of bone required large incisions (upwards of 6 cm in length) and a considerable amount of muscle be cut and stripped away (retracted) from the bone for an "open" visualization of the bone and access thereto for the placement of the fasteners and instrument implantation. Although this so-called "open" surgical technique has successfully treated non-unions, instability, injuries and disease of the spine, it is not without disadvantages. Given the invasive nature of this technique, a lengthy healing time and considerable post-operative pain for the patient is common.

In response to aforementioned drawbacks, the surgical arts have developed minimally invasive systems and procedures intended to replace the more traditional open surgeries. Obviously, a less extensive system and procedure will eliminate the need to perform much of the cutting and stripping of muscle, resulting in reduced recovery time and less post-operative pain. As a result, percutaneous procedures have been developed which insert instruments and perform operations through small skin incisions, usually between 1.5 and 5 cm in length, thereby reducing soft tissue damage. However, smaller skin incisions and smaller surgical fields require more novel and innovative approaches to perform these complicated surgeries.

One such example of a minimally invasive system is the SEXTANT Spinal system by Medtronic (Memphis, Tenn.). This device is comprised of two basic components, screw extenders, and the rod inserter, which results in an instrument that looks like a sextant used in naval navigation. The device is an insertion tool that allows fasteners and interconnecting means to be applied to the spine in a minimally invasive manner. The screw extenders are long shafts used to deliver and attach screws to the vertebrae through small skin incisions. During surgery, these extenders protrude outside the body, allowing the surgeon to arrange and join their ends so that the rod inserter may be attached. The rod inserter is an arc-shaped arm that swings along a fixed axis and pushes an interconnecting rod though the skin and muscle and into the heads of the implanted fasteners (pedicle screws).

While the aforementioned technique is adequate when the fastening means are well aligned, it fails to deliver the rod when one of the screws is misaligned. Moreover, the interconnecting rod must be pushed by the surgeon along a fixed arch and cannot be directed around neural structures or bony obstructions. One consequence of forcibly pushing the rod through the fastening means is the possibility of collision between the rod and a bony obstruction causing a piece of bone to break off resulting in possible neurological damage. Another common problem is the interconnecting rod becoming disengaged from the rod inserter. When either of these incidents happens, additional surgery is often required to remove the bone fragment and rod from the wound. This may result in the surgeon abandoning the minimally invasive approach and reverting to a traditional approach. Current spinal implant systems do not allow the contour of the rod to match the normal curvature of the surrounding anatomy and such systems are not customizable to meet the individual anatomical variables that each patient presents.

In order to help avoid damaging sensitive anatomy and expedite implant assembly, various image-based navigation systems have been employed which utilize patient images obtained prior to or during the medical procedure to guide a surgeon during the surgery. Recent advances in imaging technology have produced detailed two and three dimensional images using optically guided, fluoroscopic guided, and electromagnetic field based systems. These image-based systems have also been used in combination with the previously described "open" surgeries. One significant problem with most image-based systems is that the radiation generated is transmitted to the patient and surgical staff, which may result in physiological damage over time. Also, the cost and portability of this equipment continue to be an issue. In addition, these systems often require the surgeon undergo extensive training to operate correctly.

Accordingly, a need exists in the surgical arts for a system and minimally invasive procedure capable of providing optimal mechanical support and bony fusion, while reducing the likelihood of bone damage and neural functioning when compared to the currently available interconnecting elements. It is also desirable to provide a surgical procedure that can be performed in conjunction with, but does not require, an image-based tracking system.

PRIOR ART

Although there are numerous patents directed to systems and methods for insertion of a stabilizing implant at a selected area of an anatomy, the prior art nevertheless fails to teach a targeting system for the insertion of an implant using minimally invasive techniques having a decreased risk of causing damage to neural structures or bony obstructions using minimal, if any, radiation exposure to the patient and/or surgeon.

For example, U.S. Publication No. 2005/0085714 to Foley et al., discloses a method and apparatus for percutaneous and/or minimally invasive implantation of a construct (e.g., spinal implant). The construct may be implanted using a navigation system for planning and execution of a procedure. A plurality of portions of the construct may be interconnected using locations and paths determined and navigated with the navigation system. The navigation system utilizes optical or electromagnetic localization to determine the precise location of a selected implant construct or instrument. An optical localizer can be positioned relative to an extender attached to a screw. Alternatively, a coil may be positioned in an electromagnetic (EM) field such that the position of the coil may be determined by sensing the induced voltage. A computer is used to form a plan prior to implantation of the construct and thereafter track the various portions of the construct during insertion. The plan and the tracking of the surgery are displayed on a monitor to provide guidance to the surgeon.

U.S. Publication No. 2005/0277934 to Vardiman, discloses a minimally invasive spinal fixation system used for spinal arthrodesis (bony fusion) or motion preservation. The system comprises a plurality of pedicle screws, including a first screw placed into a first vertebral body, and a second screw placed into a second vertebral body, a connector for attaching to the first and second screws and, a removable guide for percutaneously attaching the connector to the first and second screws. According to one embodiment, detectional spheres are positioned on the head of screw extenders and on the handle of the rod insertion tool. A comparator calculates the relative position of the insertion tool handle with respect to the screw extenders and provides a visual display for the surgeon.

U.S. Pat. No. 6,236,875 to Bucholz, discloses surgical navigation systems including reference and localization frames. The system generates an image representing the position of one or more body elements during the procedure using magnetic resonance imaging (hereinafter, MRI) or computed tomography (hereinafter, CT) scan images taken prior to the surgery. The body elements and their relative position are identified during the procedure. The position of the known body elements can then be manipulated using a computer to the relative position of the patient during the surgery. The manipulated data can then be utilized to guide the surgeon for implantation.

U.S. Pat. No. 6,226,548 to Foley et al., discloses an apparatus and procedures for percutaneous placement of surgical implants and instruments such as, for example, screws, rods, wires and plates into various body parts using image guided surgery. The invention includes an apparatus for use with a surgical navigation system, an attaching device rigidly connected to a body part, such as the spinous process of a vertebra, with an identification superstructure rigidly but removably connected to the attaching device. This identification superstructure, for example, is a reference arc and fiducial array which accomplishes the function of identifying the location of the superstructure, and, therefore, the body part to which it is fixed, during imaging by CT scan or MRI, and later during medical procedures. The system utilizes emitters such as light emitting diodes (hereinafter, LEDs), passive reflective spheres, acoustics, magnetics, electromagnetics, radiologic, or micro-pulsed radars for indicating the location of a body part to which the emitter is attached.

U.S. Pat. No. 7,011,660 to Sherman et al., discloses a brace installation instrument and method for the stabilization of bony structures. The installation instrument is sextant-type tool with anchor extensions coupled to the anchors. The instrument is movable with respect to the anchors to position a brace in a position proximate to the anchors. The brace can be indexed for insertion at a predetermined orientation with respect to the installation instrument.

All of the aforementioned prior art disclose a system which utilize an implant insertion means to forcibly push the surgical implant or instruments to the target area in vivo. This increases the possibility of pathway divergence and/or damage to neural and vascular structures. What has been heretofore lacking in the prior art is a simple and economical system and procedure for the accurate and precise placement of surgical implants and/or instruments at a target area while providing a decreased risk to neural and vascular structures. Moreover, none of the aforementioned references provide audible and/or tactile feedback to the surgeon that indicates the target area has been reached.

SUMMARY OF THE INVENTION

The instant invention is related to a magnetic targeting system suitable for guiding a biocompatible device, (implant, surgical instrument) to a target area within the body (in vivo), be it a tumor or implantation point for a fastening means. The system includes a targeting member that includes a steering material. The targeting member is attached at one end to the biocompatible device. The system also includes at least one anchoring member constructed and arranged to secure to a target area in vivo at one end and the other end constructed and arranged for inclusion of a magnetic material effective for influencing the traversal of the steering material in vivo. The magnetically influenced anchoring member interacts with the steering material of the targeting member such that the connected biocompatible device is positionable relative to the target area.

It therefore an objective of the instant invention to provide a system that minimizes soft tissue damage and provides less post-operative pain.

It is a further objective of the instant invention to provide a targeting system that provides real time targeting by providing feedback as to the position of the biocompatible device.

Yet another objective of the present invention is to disclose a feedback system that utilizes audio and/or tactile feedback to indicate to the surgeon when the target area is reached.

Another objective of the present invention is to provide a magnetic targeting system that can penetrate tissue without being distorted or causing physiologic damage, unlike x-rays.

Still a further objective of the invention is to teach a targeting system which allows for shorter surgery, decreased x-ray exposure, and fewer complications for the patient.

Yet another objective of the instant invention is to provide a targeting system that is simple to operate to reduce the training the surgeon must undergo for operation of peripheral systems.

These and other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments illustrate various objects and features thereof.

BRIEF DESCRIPTION OF THE FIGURES

FIGS. 16A through 16L illustrate the various steps the various steps necessary for installation of the surgical implants where the connecting member between the fastening members is pushed into place.

FIGS. 18A, 18B and 18C are side views of another alternative embodiment of a magnetic catcher.

FIG. 19A is a perspective side view of a device used to determine the shape of the rod prior to insertion into the patient.

DETAILED DESCRIPTION OF THE INVENTION

Detailed embodiments of the instant invention are disclosed herein, however, it is to be understood that the disclosed embodiments are merely exemplary of the invention, which may be embodied in various forms. Therefore, specific functional and structural details disclosed herein are not to be interpreted as limiting, but merely as a basis for the claims and as a representation basis for teaching one skilled in the art to variously employ the present invention in virtually any appropriately detailed structure.

Figure 1:
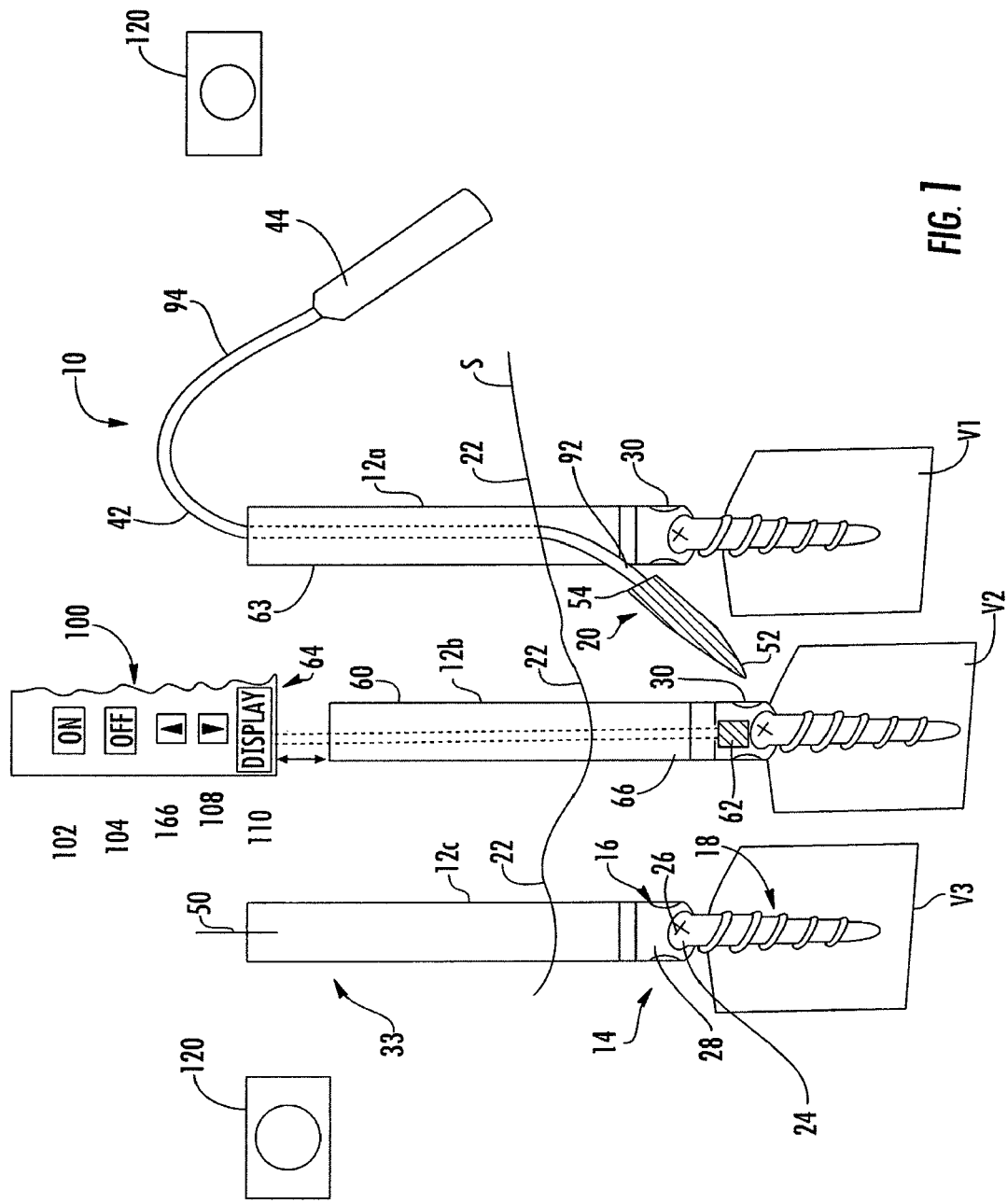
FIG. 1 illustrates a partial side view of a portion of a patient's spine which includes magnetic targeting system according to a preferred embodiment of the invention.
Figure 2:
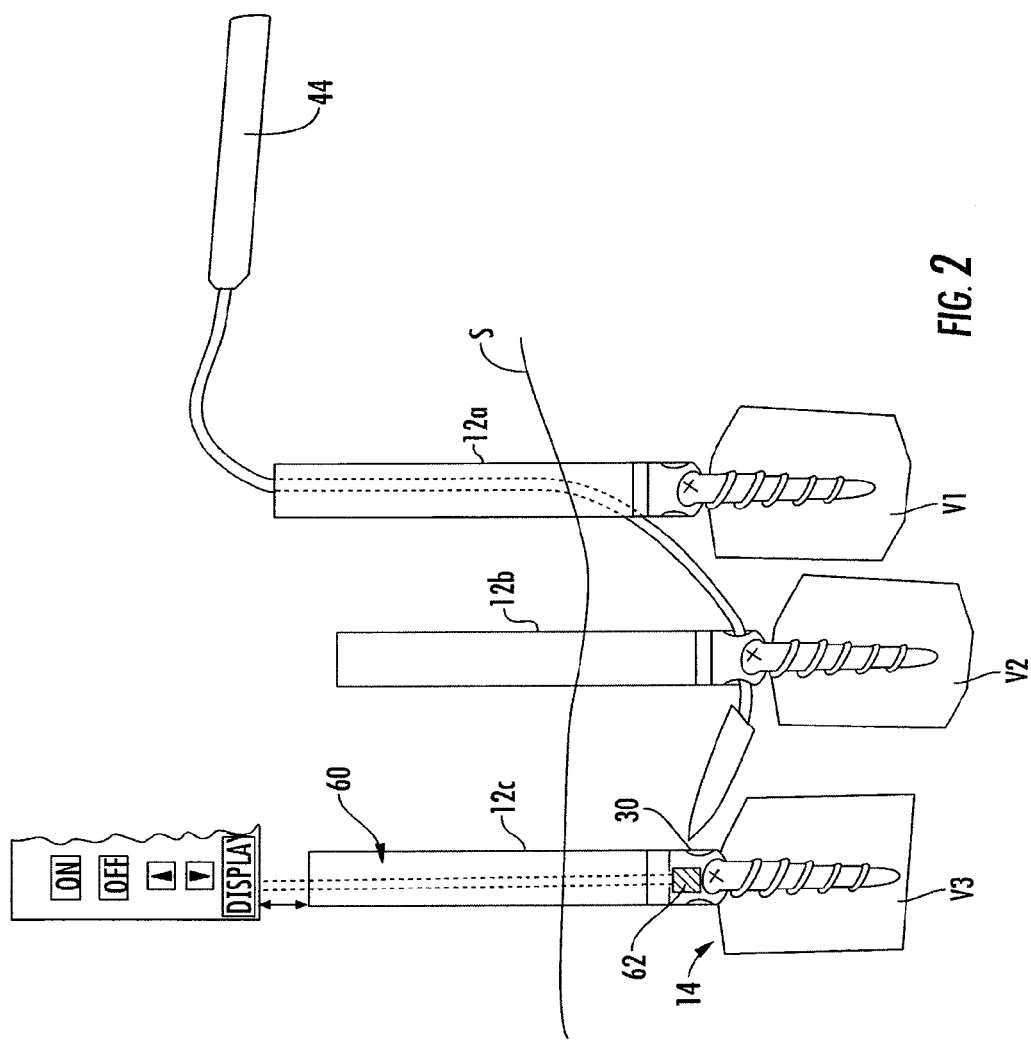
FIG. 2 is the magnetic targeting system as shown in FIG. 1, illustrating the targeting member with attached tethering means threaded through an anchor member.
Figure 3:
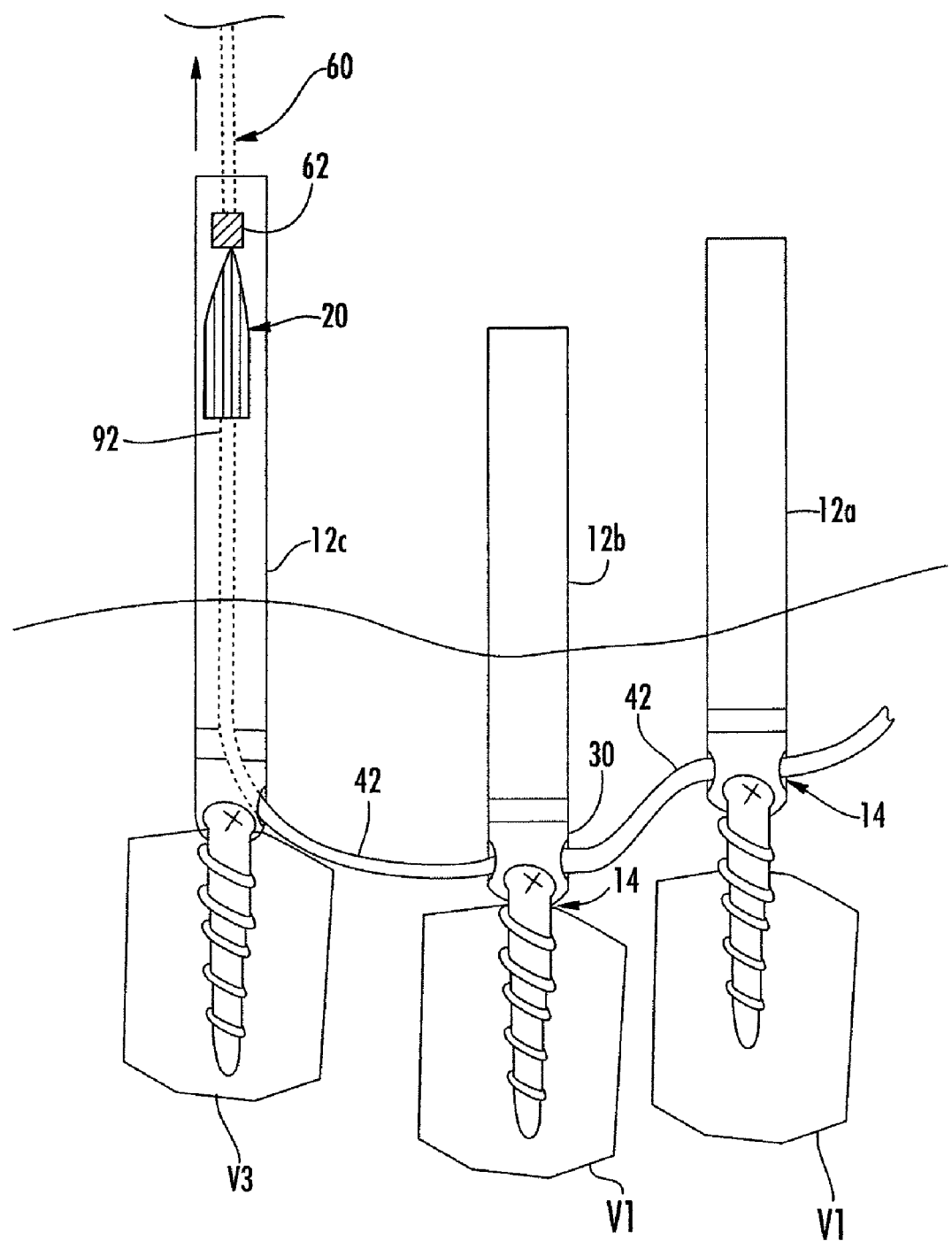
FIG. 3 is the magnetic targeting system shown in FIG. 1, illustrating the targeting member being removed from the interior of the patient through the last extender.

Referring now to FIGS. 1-9 which illustrate the magnetic targeting system 10 of the present invention suitable for facilitating navigation to a target area, wherein like elements are numbered consistently throughout. FIG. 1 shows a plurality of anchoring members 14 (also referred to as fastening means). The anchoring members are depicted here as multi-axial pedicle screws, each removably attached to an extender 12a, 12b, and 12c. These screws have a proximal end 16 and a distal end 18. The proximal end includes head portion 24 with a tool opening 26 configured to receive a driving tool (not shown). The distal end includes a threaded shank designed to secure to a selected target area located inside the body of a patient (in vivo), shown here as consecutive spinal vertebrae V1, V2, V3. Although the target area is exemplified here as vertebrae in a partial spinal column the target area may be located anywhere in vivo.

Figure 5:
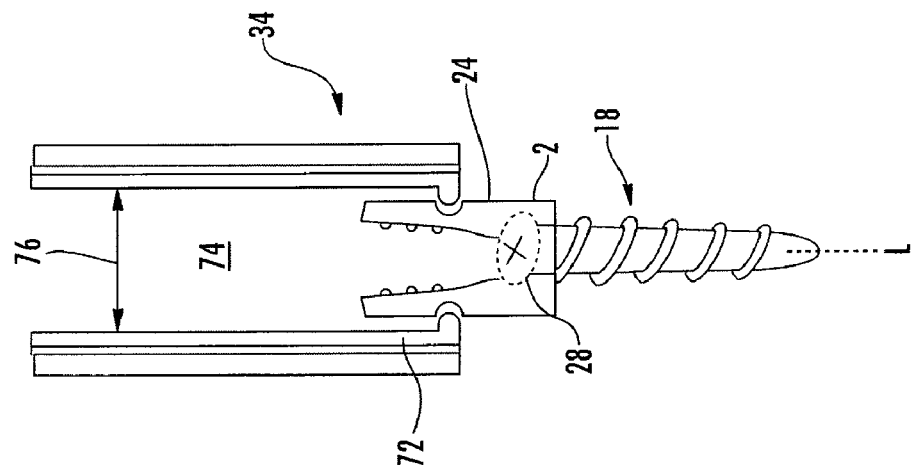
FIG. 5 is a partial cross-sectional view of a portion of the extender removably attached to the connector portion of the multi-axial screw in accordance with one embodiment.

The screw shown here is a multi-axial screw where the proximal end of the screw may include a connector 28 rotatably connected to the head portion 24 of the screw. That is, the connector is capable of 360 degree rotation relative to the threaded shank 27 of the screw along the axis L of the shank and angular motion defined by the angle a (FIG. 5). One example of a suitable multi-axial screw is described in U.S. Pat. No. 5,797,911, herein incorporated by reference. Although a multi-axis is exemplified herein, it is contemplated that a fixed axis screw may be used. Fixed-axis screws do not include a rotatable connector 28. Other means for anchoring are also contemplated herein, some of which include, clamps, hooks, claws, bolts, or the like. Moreover, the shank of the anchor member may or may be not be cannulated, as is known in the art.

Figure 6:
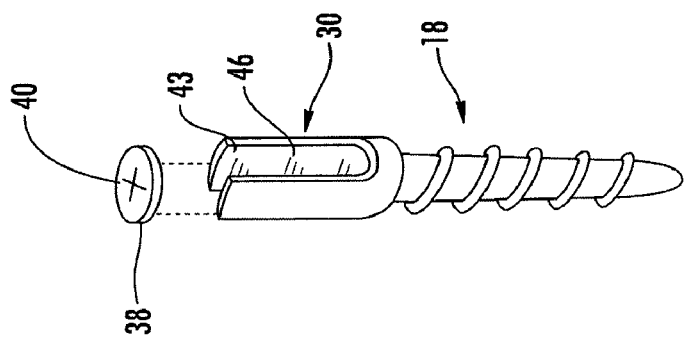
FIG. 6 is an upper perspective view of a multi-axial screw that can be used in system of the present invention.

As shown in FIGS. 5 and 6, the connector portion of the screw is constructed and arranged to form a passageway 30 designed to removably receive implants of various sizes. The connector portion includes an opening 43 constructed and arranged to receive a set screw 38. As shown in FIG. 6, the head portion includes threaded interior sidewalls 46 designed to mate with external threads 38 formed on the set screw. Thus, as the set screw is threadably lowered along the connector portion of the screw the passageway 30 in the connector is narrowed. The passageway is narrowed until the exterior surfaces of the biocompatible device 44 (shown here as interconnecting rod, see FIGS. 1-4) are sandwiched between the upper portion of the screw head 24 and the set screw. This acts to reliably secure the biocompatible device onto the screw. As with the head of the screw, there should be a tool opening 40 configured to receive a driving tool (not shown) inserted within the interior portion 74 of the extenders. The driving tool is well known in the surgical arts and is used to rotatably secure the set screw to the desired position within the interior of the connector.

As discussed above, the distal end 34 of each of the hollow extenders 12a, 12b, 12c are removably attached to the screws by any appropriate means known in the art. For example, the extender may include a depressible member (not shown) located at the proximal end 33 of the extender that is operatively connected to an internal clamping member located that the distal thereof. The clamping member is capable of engaging and disengaging the connector portion of the screw. One example of a suitable extender which could be used in the present invention is disclosed in U.S. Pat. No. 7,011,660, herein incorporated by reference. The extender may also be able to rotate the connector of a multi-axial screw relative to the shank to facilitate the threading of the interconnecting rod there through.

The extenders should be made of a substantially rigid biocompatible material and have a length dimension (along its longitudinal axis 50) that allows the proximal end 33 to protrude a distance outside of the percutaneous exposure 22 created through the outer skin S of the patient. According to a preferred embodiment, at least the first extender should have a "c-shape", as seen along an axis transverse its longitudinal axis, thereby defining a slot 63 that extends along its longitudinal axis 50 and into the patient when attached to the screw. The slot should be sized to allow the targeting member to exit, so that it is able to be delivered percutaneously, as shown in FIG. 1. The interior dimension 76 of the extenders should be such that they are capable of receiving the appropriate driving tool (not shown) used to engage the screws and set screws. In addition, the interior dimension of the extenders should be able to accept a removable magnetic device for magnetically influencing the anchor members 14, as described further below.

Referring again to FIGS. 1-4, a targeting member is shown attached to biocompatible device 44 by a tethering means 42. The targeting member has a first end 52 and a second end 54. The first end is designed to penetrate the tissue and is shaped to enlarge the opening while creating a pathway through the tissues as the targeting member is advanced in vivo. At least the first end of the targeting member is composed of a steering material capable of being magnetically influenced, as described hereafter.

Figure 7A:
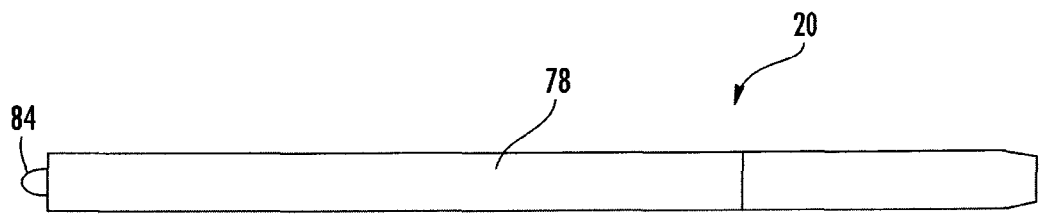
FIGS. 7a thru 7e illustrate various embodiments of the targeting member used in the instant invention.
Figure 7B:
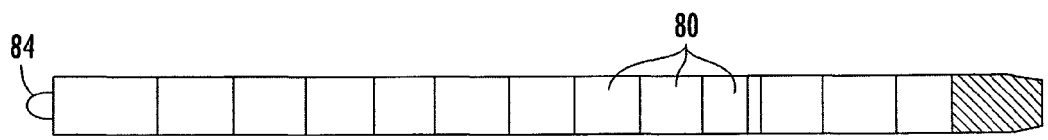
Figure 7C:
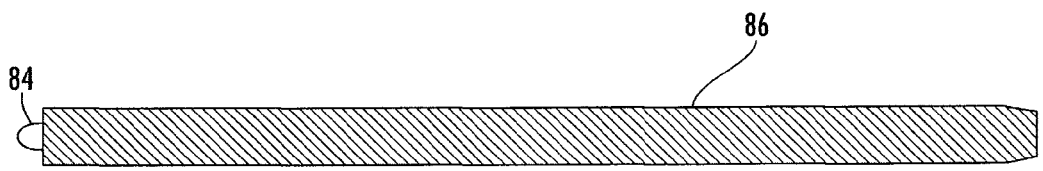
Figure 7D:
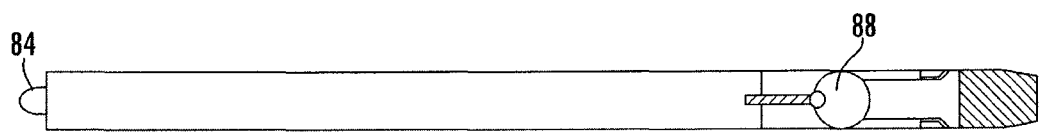
Figure 7E:
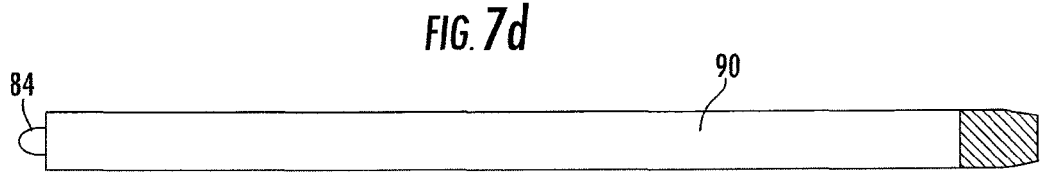

As shown in non-limiting embodiments of FIGS. 7a-e, the targeting member 20 may be made from a flexible, semi-rigid, or rigid material, each includes the steering material 84 located on the first end. FIG. 7a illustrates an embodiment of a semi-rigid targeting member in the form of rod-like member with steering material 84 disposed on its first end 52. The first portion 78 of the rod is made of a flexible material capable of safely colliding with bony or neural obstructions without causing damage. FIG. 7b illustrates another flexible rod formed of a plurality of rigid consecutive segments 80 through which the tethering means 42 extends to the first end (not shown). When the surgeon pulls the tethering member at the second end taunt, the segments are forced together and little movement is permitted between the segments. In the embodiment of FIG. 7c, the entire targeting member is composed of or coated with a second biocompatible steering material 86. FIG. 7d illustrates another embodiment wherein the targeting member includes a ball joint 88 attached to the tethering means. As with the embodiment of FIG. 7b, the tension in the tethering member controls the amount of pivot at the ball joint. Thus, when tension is released the rod comes flexible and the first end of the targeting member pivots on the ball. Alternatively, when the tension is reapplied to the tethering means, the rod is solid again. This way the surgeon is able to safely guide the targeting member around neural and bony obstructions as it moves through the body. Lastly, FIG. 7e depicts a rigid rod-like member formed from solid biocompatible material 90.

The tethering means 42 may be made of any flexible or semi-flexible biocompatible material capable of allowing the device to navigate around neural and bony obstructions without damaging them. Examples of suitable tethering means may be in the form of a cable, cord or ligament. Moreover, the tethering means may be formed of a cannulated or solid member. As discussed above, the first end 92 of the tethering means is attached to the second end 54 of the targeting member by any means of attachment known in the art. Similarly, the second end of the tethering means is attached to the biocompatible device 44 by any means of removable connection known in the art. For example, the biocompatible device and tethering means could include corresponding threads that the surgeon can rotate to disconnect the tethering means from the biocompatible device.

According to a preferred embodiment, the biocompatible device is shown as an implantable interconnecting rod. The rod may be rigid, semi-rigid or flexible. Rigid rods are usually preferred for providing the necessary stability during the healing process and arthrodesis, however, flexible rods have been found to provide for arthrodesis while allowing some movement between bony structures that have been interconnected to preserve some motion. Moreover, like the tethering means the biocompatible device may also be solid or cannulated.

Although the interconnecting rod is shown in FIGS. 1-4 as interconnecting two pedicle screws, the surgeon could use any appropriately sized rod having a length dimension capable of interconnecting three or more fastening means co-linearly implanted along multiple vertebrae. It is also within the purview of the invention that any sized rod having various widths or diameters could be used so long as it is capable of stabilizing the bony structures for bony fusion. Although a rod-like member is exemplified herein, other such biocompatible devices known to one skilled in the art are also contemplated, for example, plates, clamps, etc.

Figure 4:
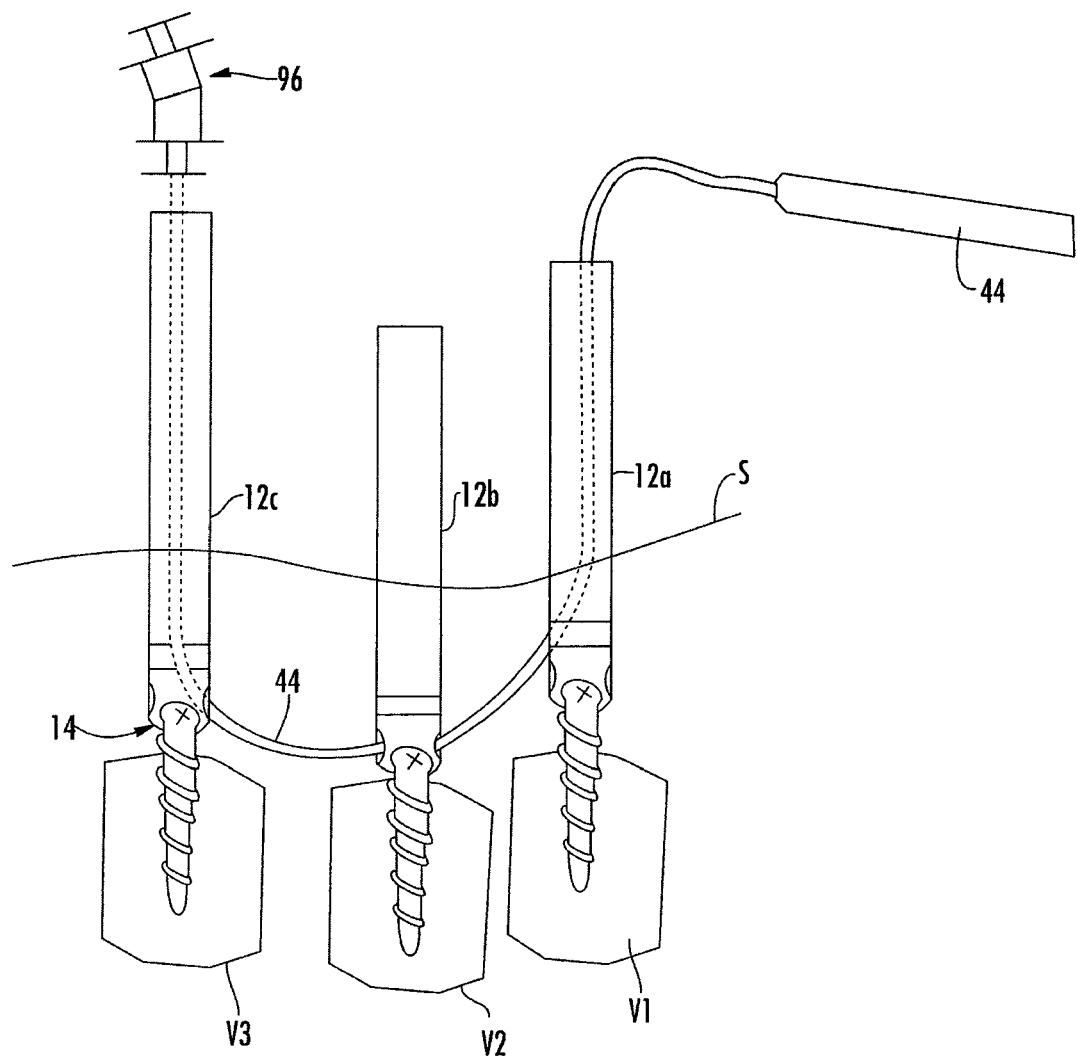
FIG. 4 is the magnetic targeting system as shown in FIG. 1, illustrating the insertion of the biocompatible device between adjacent vertebrae.

FIG. 4 illustrates a hollow or cannulated flexible biocompatible device in fluid communication with a cannulated tethering means. According to this embodiment, once the rod has been properly inserted into the desired location, the surgeon can use an insertion means 96 (syringe or the like) to supply a biocompatible hardening material (e.g., cement, carbon, bone matrix) through the tethering means and into the interior of the hollow rod. Although not required, the biocompatible device might also be made permeable and used to deliver constituents supplied by the insertion means to the target area (e.g., bone growth/fusion material, medication, curing material, etc.).

As shown in FIGS. 1-4, each of the proximal ends of the extenders 12a-c protrude outside of the patient's skin through percutaneous incisions 22 so that the surgeon is able to insert instrumentation through the extender's interior portion to access the screw secured to the target area (vertebra). The extenders also enable the surgeon to insert the magnetic device or wand 60 into the selected extender to a position proximate the corresponding anchor 14. The magnetic device includes a proximal 64 and a distal end 66. Magnetic material 62 is attached at the distal end of the device and the proximal end may include a grip 100 (not required) for the surgeon to hold the magnetic device. The wand should be sized to extend the length of the extender.

Figure 9:
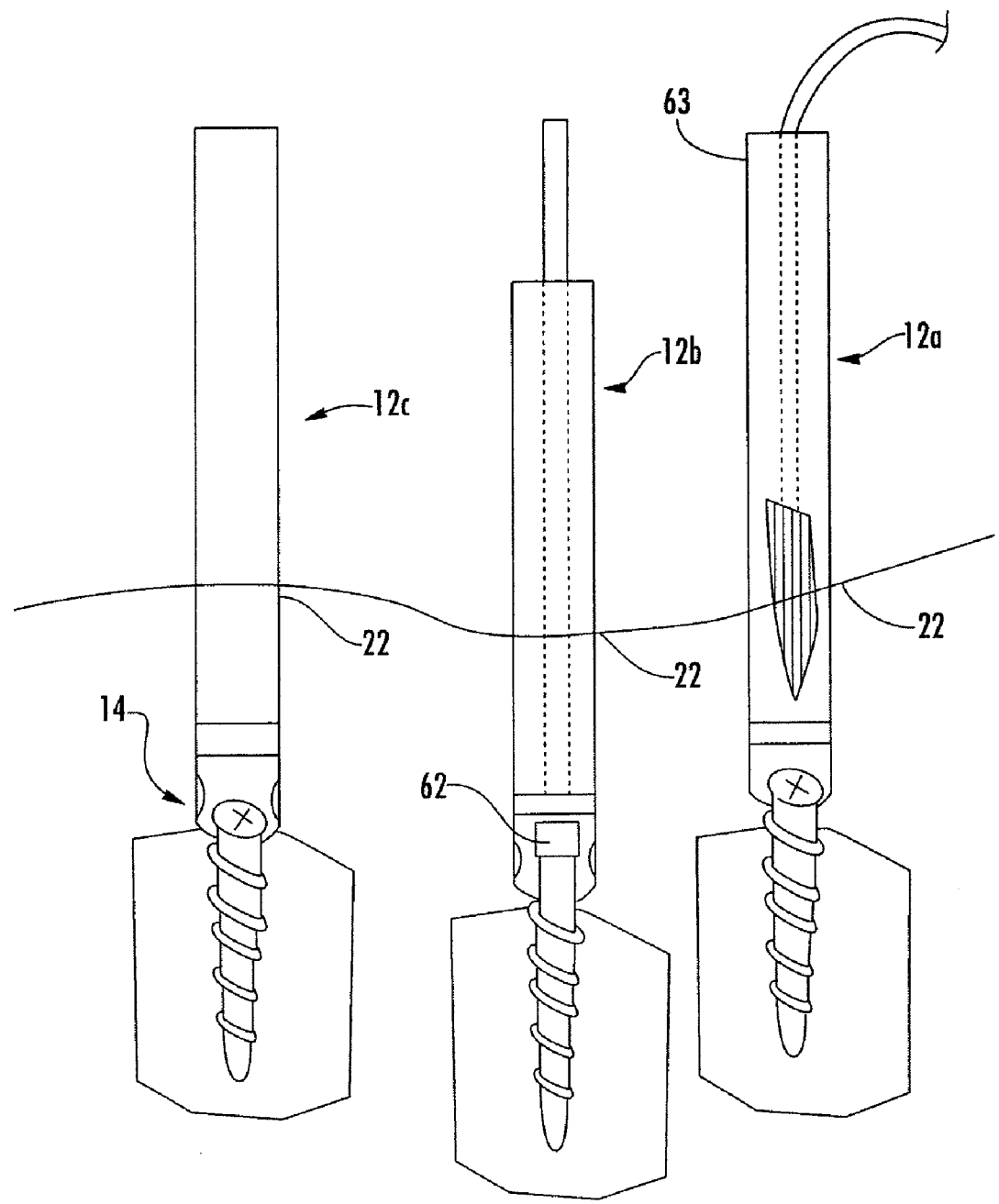
FIG. 9 illustrates a partial side view of a portion of a patient's spine which includes magnetic targeting system according to another embodiment of the invention using a permanent magnet.

The "magnetic material" 62 as used herein refers to either a permanent magnet (as shown in FIG. 9) or an electromagnet (shown in FIGS. 1-4) which generates a magnetic field capable of influencing the steering material in the targeting member in vivo. As is known in the art, an electromagnet is a magnet in which the magnetic field is produced by a flow of electrical current. One example of a suitable permanent magnet is a Neodymium Iron Boron (NdFeB) magnet since it is powerful and has been approved by the U.S. Food and Drug Administration (FDA) for internal use. Another example is the use of a recently developed biocompatible non-metallic magnet, or plastic magnet, made from the polymer PANiCNQ which is combination of emeraldine-base polyanailine (PANi) and tetracyanquinodimethane (TCNQ).

The "steering" material in the target member, as used herein, refers to any material capable of being influenced by the magnetic material 62. For example, the steering material may include any magnetically attractive material or alloy, (e.g. steel, iron, etc). The steering material may be the same or different than that used for magnetic material 62 so long as it is capable of being influenced, e.g., attracted or repelled. Moreover, either or both the magnetic material and the steering material may be coated with any suitable biocompatible element, such as plastic. The type, shape, and size of the magnetic material and steering material should be suitable for internal use in patients and provide the optimal magnetic field. Magnetic fields are used herein for navigating in vivo since these fields can penetrate human tissue and bone without being distorted similar to x-rays, but without the danger of radiation and physiologic damage.

According to a preferred embodiment shown in FIGS. 1-4, the magnetic material employs an electromagnet having controls located in the handle or grip 100. At a minimum, the controls should include buttons and associated circuitry that will allow the surgeon to turn the electromagnet on 102 and off 104. Preferably, the controls also include buttons and circuitry capable of increasing 106 or decreasing 108 the strength of the magnetic field generated by the electromagnet and/or switch between polarity (north and south poles). As is known, the polarity of a magnet allows it to attract or repel magnetic material within its magnetic field. The controls can also include a display 110 used to indicate the strength of the magnetic field being applied.

The method of using the magnetic targeting system 10 of the present invention is described in accordance with the embodiment depicted in FIGS. 1-4. First, the anchoring member (shown here as the multi-axial pedicle screw) is inserted into the desired target area (shown here as vertebra), as is known in the surgical art. The screw may be removably attached to the distal end of the extender before or after attachment of the screw to the selected vertebrae. Once attached, the surgeon inserts the targeting member into the proximal end of the extender which protrudes outside of the percutaneous exposure 22. The magnetic device is inserted into the next vertebra V2 which includes the anchoring member (extender and screw), shown here as 12b. The magnetic material 62 is disposed proximate the target area via wand 60. According to this example, the magnetic material is placed inside the connector portion of the screw, this may be done prior to, during, or after the targeting member is inserted into the extender. If an electromagnet is used, the surgeon will switch on the electrical current to begin generating an attractive magnetic field when in the proper position in vivo. If a permanent magnetic is used for the magnetic material 62, the surgeon simply places it inside the connector portion of the screw, see FIG. 9.

As a result of the attractive magnetic field, the steering material in the targeting member is pulled through the extender slot 63. The strength of the magnetic field generated by the magnetic material should be capable of pulling the targeting member (including attached tethering mean) toward the magnetic member such that the pointed first end penetrates the tissue and creates a pathway through the tissues as the targeting member is advanced toward the magnetic material. The use of the magnetic field to guide the targeting member, as compared to forcibly pushing the targeting member, as disclosed in the prior art, reduces the probability of damaging neural structures or breaking bony obstructions encountered along its path.

Once the targeting member has reached the magnetic material 62 positioned inside the connector portion of the screw, the surgeon removes it from the anchoring member and places it into the next anchoring member (extender and screw), shown here as 12c attached to vertebra V3. The aforementioned procedure is then repeated inside anchoring member 12c. If an electromagnet is used, the electricity along the magnetic member is turned on and the strength of the magnetic field generated pulls the targeting member through the passageway 30 of the screw secured to V2 and toward the magnetic member located inside the screw secured to V3, see FIG. 2. If a permanent magnet is used, the surgeon simply places the distal end inside the connector portion of the anchor.

As described before, the pointed first end of the target member penetrates the tissue and creates a pathway through the tissues as it moves toward the magnetic material. This technique of threading through the screw does not require the surgeon to try to align multiple pedicle screws along the fixed path of the rod. Moreover, the continuous magnetic attraction of the targeting member toward the pedicle screw reduces the possibility that the target member will be diverted by structures in the anatomical topography that may cause it to penetrate unintended areas. In addition, the present invention allows the surgeon to avoid a given anchor member. In such a circumstance the surgeon can insert the magnetic material into that extender connected to the anchor member that is to be avoided. The magnetic material maybe either a permanent magnet or electromagnet having the same polarity as that of the targeting member. This will repel the steering material of the target member from that target area.

Once the final vertebra is reached, the magnetic member is used to pull the targeting member through the slot in the upper opening 43 of the pedicle screw and along the interior length of the extender until it reaches the proximal end protruding out of the incision. The surgeon can then grasp the targeting member and attached tethering means, see FIG. 3. The tethering means located outside the patient is then used by the surgeon to gently pull the attached biocompatible member (rod) along the path formed through the tissue by the targeting member and through the connector portion of the pedicle(s) until the biocompatible member reaches the last vertebra, as shown in FIG. 4.

If the tethering means and interconnecting rod are hollow, the user can disconnect the targeting member and releasably attach an injection means 96 thereto. The injecting means can be used into supply any suitable any flowable, biocompatible material inside the rod. One example of a suitable biocompatible material includes at least one a hardening material that will cause the rod to become rigid.

Otherwise, the rod might be filled prior to the introduction of a hardening material. For example, the rod might contain ferroelectric material that allows the rod to remain flexible during insertion process until exposed to an electric current. This is particularly suitable if used in conjunction with the electromagnet embodiment previously described. Once the flexible rod is positioned at the final desired location (secured to pedicle screws), the rod may then be exposed to electric current in the electromagnet by inserting the magnetic means into the extenders. The electric current causes the ferroelectric material to harden to make a substantially rigid rod. Thus, the contour of the rod corresponds to the natural curvature of the surrounding anatomy.

As discussed above, the connector portion of the screw is constructed and arranged to receive a set screw 32 therein. The set screw is inserted into each of the extenders and threadably attached by the driving tool (not shown) positioned in the extender and inserted in tool opening in the screw. The interconnecting rod 44 is sandwiched between the upper portion of the head and the set screw. This acts to secure the rod onto the screws. The extenders are then removed from the connector portion of the screw and the exposures closed.

Figure 8:
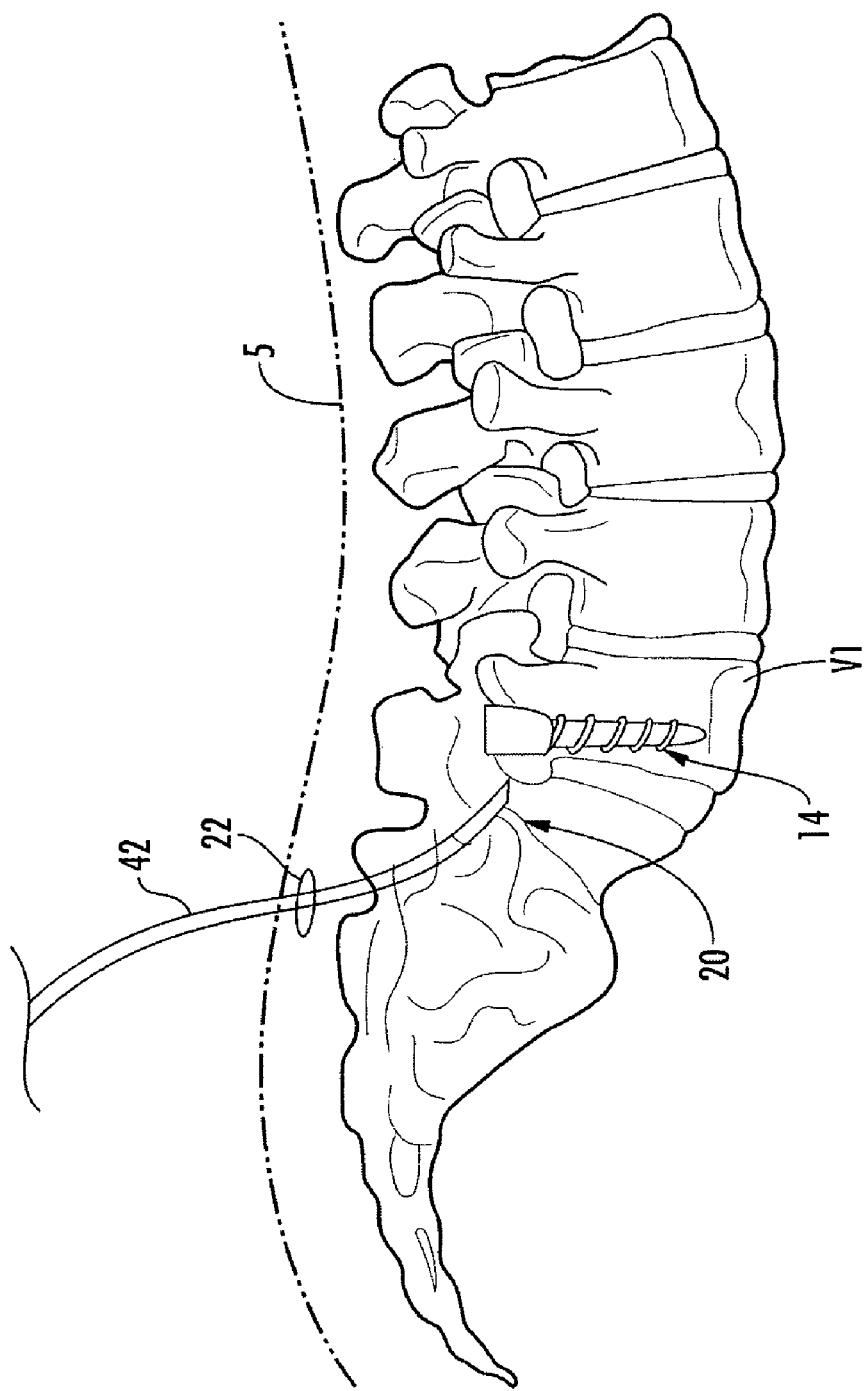
FIG. 8 is a partial side view of portion of the spine of a patient which includes the magnetic targeting system according to another embodiment illustrating the insertion of the targeting member in vivo without the use of extenders.

Referring to an alternative embodiment shown in FIG. 8, the targeting system of the present invention does not require the use of an extension member for insertion of the targeting member in vivo. The anchoring member may be implanted and the exposure closed with no external access thereto. The proximal end of the implanted anchoring member may include either a permanent magnet or a remotely controlled electromagnet, as is known in the art. Thus, the targeting member 20 may be directly inserted and fed into the body through an incision created by the surgeon. As with the previous embodiments, the magnetic portion of the anchoring member is capable of attracting or repelling the targeting member placed inside the patient.

Any of the aforementioned embodiments of the system and techniques of the present invention can employ any type of known imaging system to determine and locate placement of any of the aforementioned structures in vivo. For example, insertion of the anchor member into the bony structure can be pre-planned by CT scan, x-ray, or the imaging means known in the art.

The present system may also include a feedback system having at least one detection element 120 (two are shown in FIG. 1) disposed outside and proximate the patient to determine the position of the targeting member and/or biocompatible member in real-time. According to one, albeit non-limiting embodiment, the detection element is an audio receiver or pickup capable of audibly detecting when the targeting member and magnetic means connect or "click" together. This way, the surgeon can imagelessly determine that the targeting member has reached the magnetized portion of the anchoring member. This may be used in conjunction with a tactile sensation produced when the targeting member and magnetic means connect. This tactile sensation of the two elements meeting will be felt by the person holding the tethering means.

Figure 10:
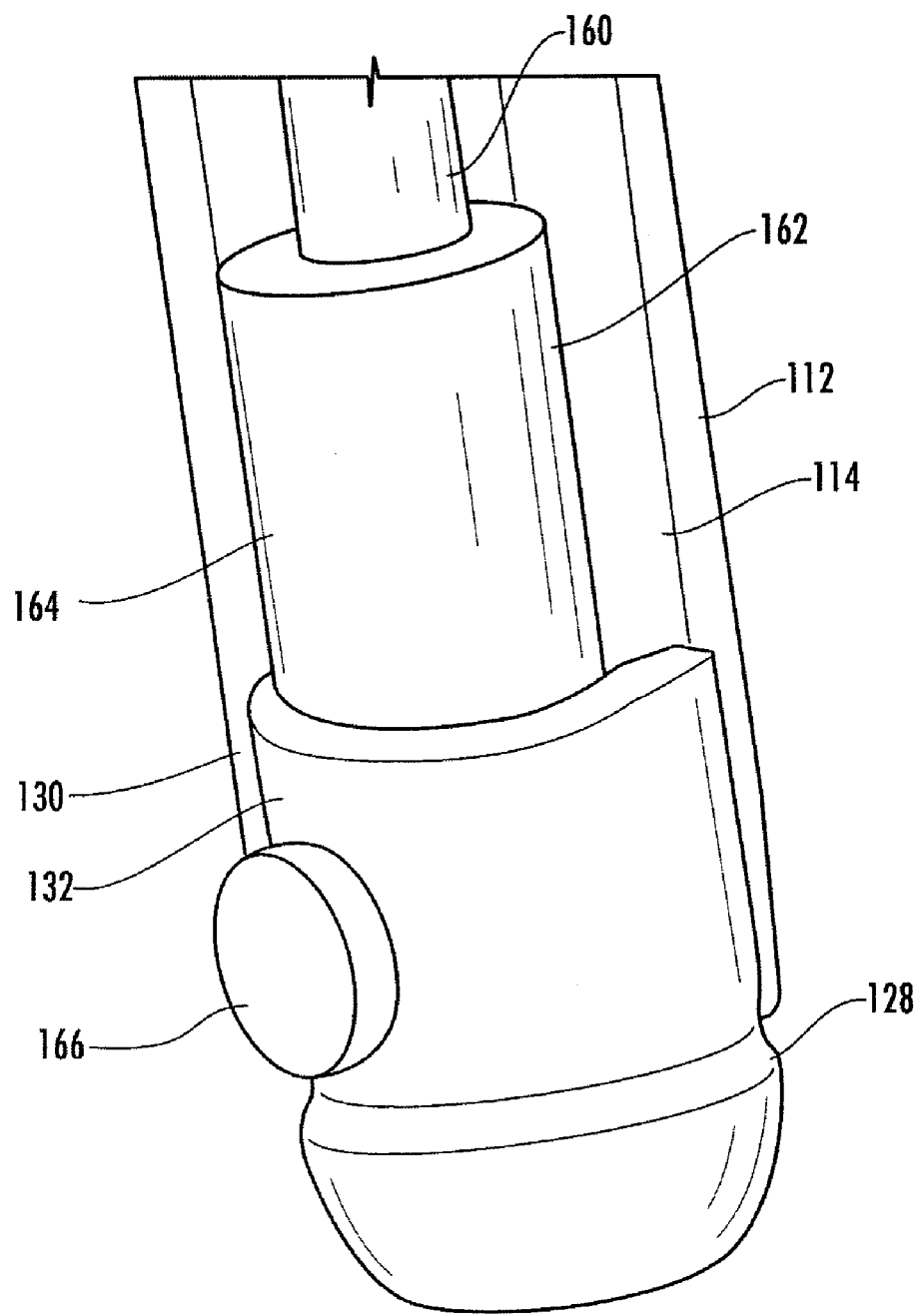
FIG. 10 is a perspective view of the magnetic device and magnetic catcher with the magnetic catcher protruding out of the extender and connector member.

FIG. 10 shows a magnetic device or wand 160 with a turnable magnetic catcher 162 located at the distal end of the wand 160. The magnetic wand 160 and magnetic catcher are sized to fit with the internal cavity 114 of extender 112. The magnetic catcher 162 is constructed from any one of the magnetic materials noted above. It includes a first cylindrical portion 164 that is positioned coincident with the longitudinal axis of the wand 162. The diameter of the first cylindrical portion 164 of magnetic catcher 162 is larger than the diameter of the wand 160 but is less than the diameter of the internal 114 cavity of extender 112. Magnetic catcher includes a second cylindrical portion 166 which is smaller in diameter than the first cylindrical portion. Second cylindrical portion 166 is generally "L" shaped and includes a vertical section that transitions into a horizontal section through a ninety degree turn. As shown in FIG. 10, the second cylindrical portion of turnable magnetic catcher 162 can be moved to position that extends outwardly of inner cavity 114 through passageway connector 130 of connector 128 and passageway 132 in extender 112 and into the body. The magnetic catcher 162 is then in a preferred position to attract and align the targeting member 20 with passageways 132 and 130.

Figure 11:
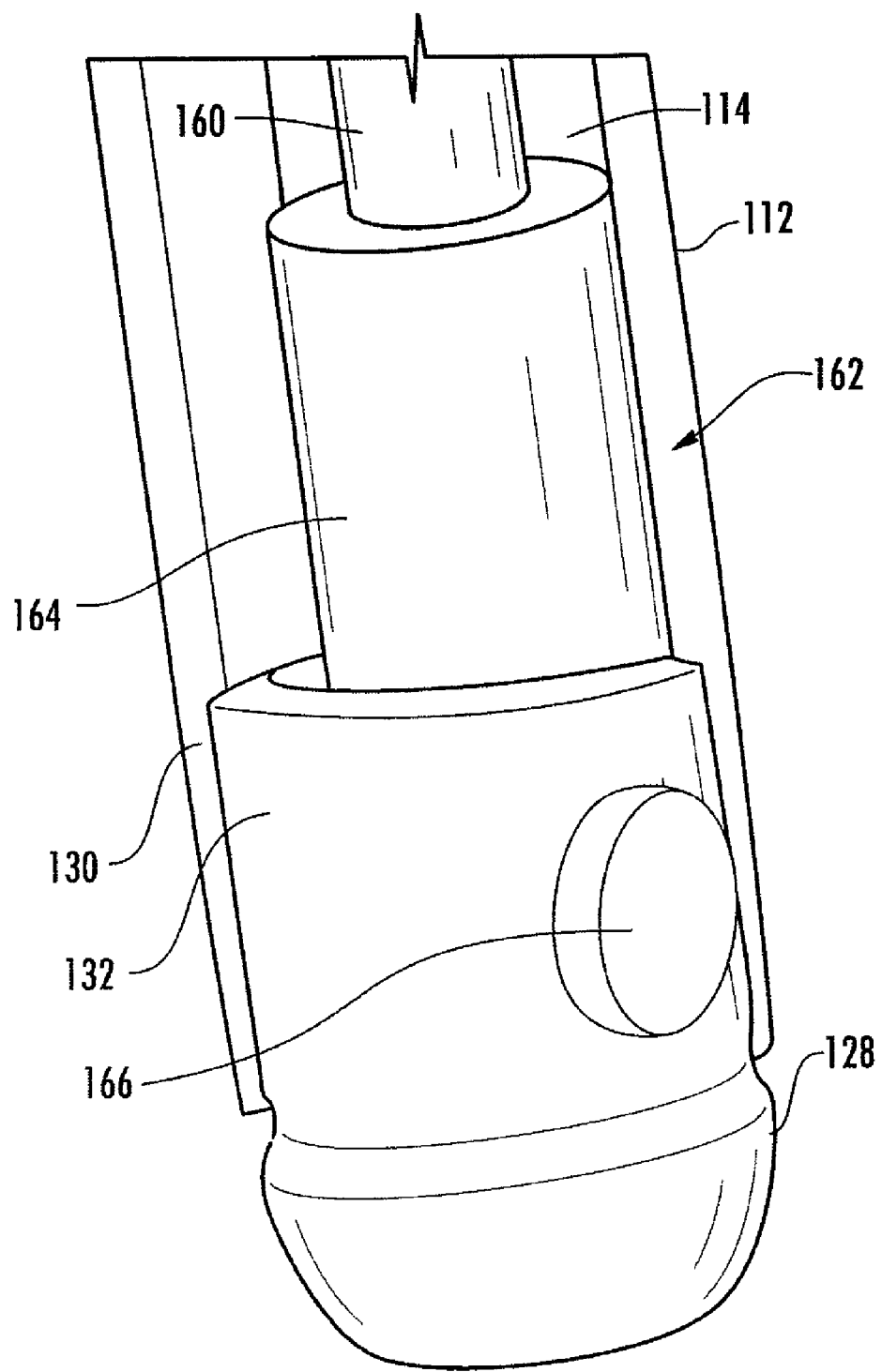
FIG. 11 is a perspective view of the magnetic device and magnetic catcher with the magnetic catcher positioned within the extender and connector member.
Figure 12:
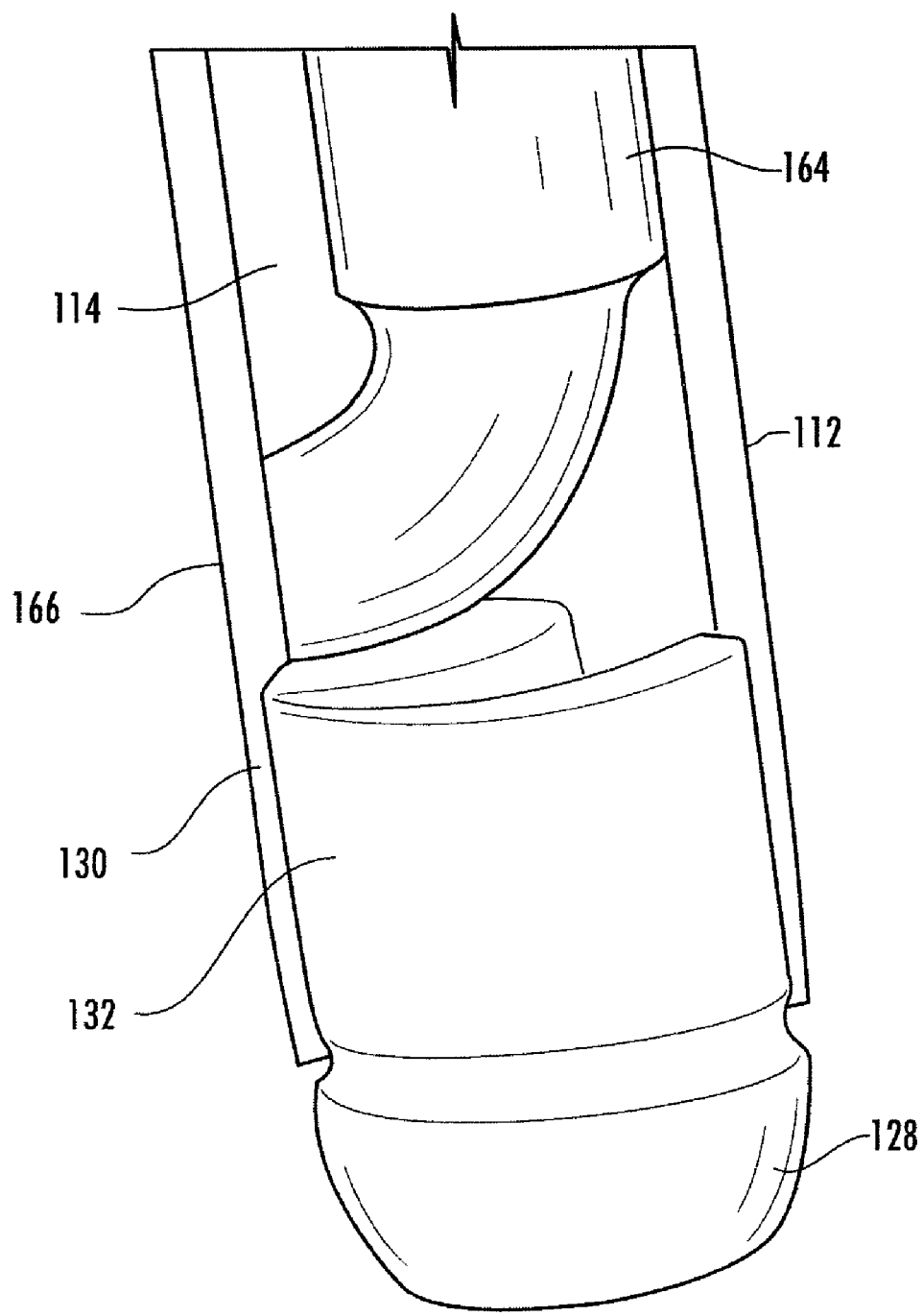
FIG. 12 is a perspective view of the magnetic device and magnetic catcher in a position in an upper portion of the extender.
Figure 13:
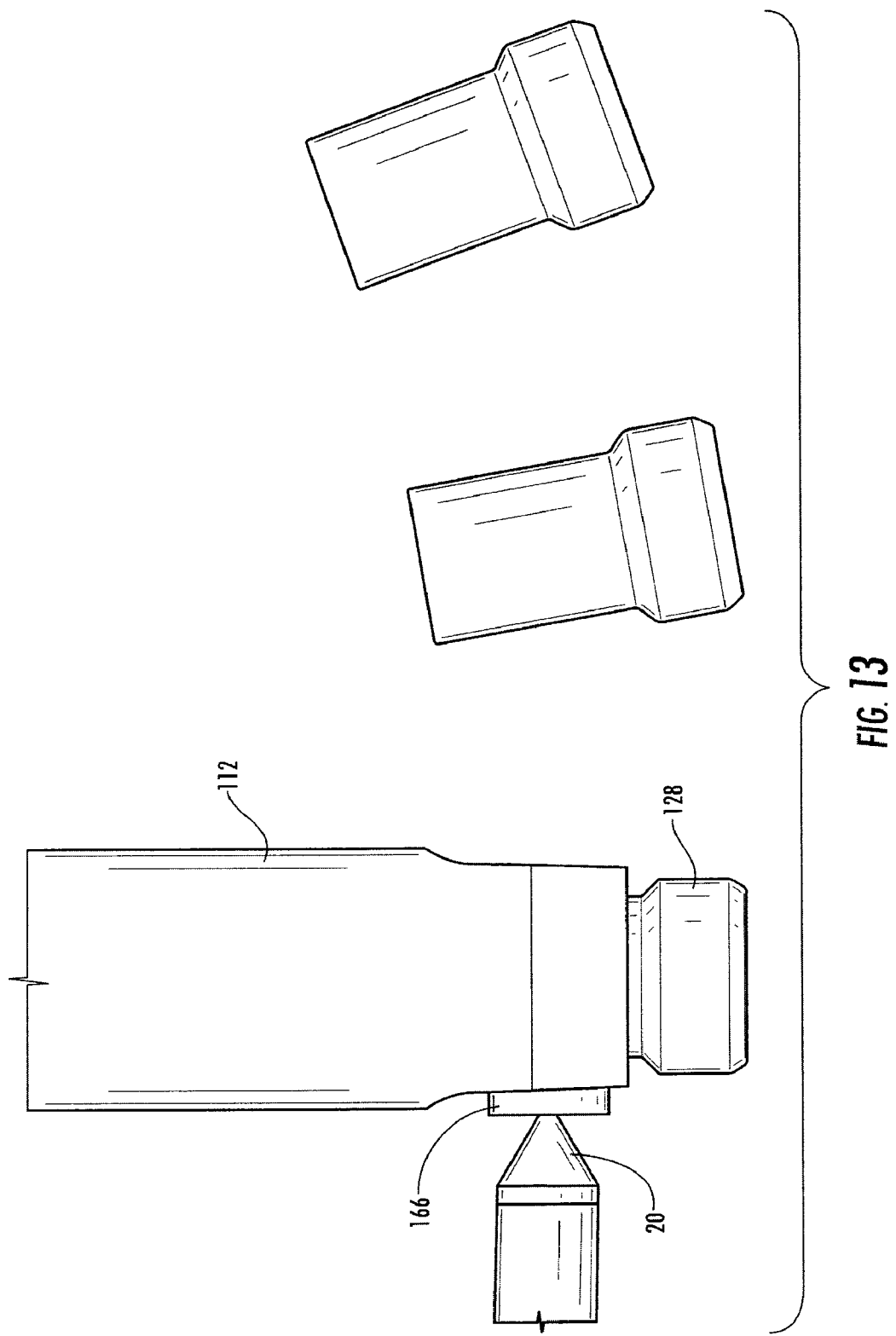
FIG. 13 is a perspective view of the magnetic catcher in contact with a target member of the first fastener.

As shown in FIG. 11 the first and second portions of magnetic catcher 162 are sized such that the magnetic device or wand 160 and magnetic catcher 162 may be inserted down to the bottom of extender 112 where the second cylindrical portion 166 of magnetic catcher 162 is aligned with passageways 130 and 132. Likewise, as shown in FIG. 12 the wand 160 and magnetic catcher 162 can be removed by pulling them up within the inner cavity 114 of extender 112. The diameter of the first cylindrical portion 164 and geometry and size of the second cylindrical portion 166 being such that the magnetic catcher 162 can be easily inserted and removed from extender 112. FIG. 13 show the relationship between magnet catcher 162 and the targeting member 20 when properly aligned. Conformation of positive engagement by repeated tactile "snap" or "click" between the magnetic catcher and the target indicates a proper alignment of the rod 144 with passageways 130 and 132.

Figure 14:
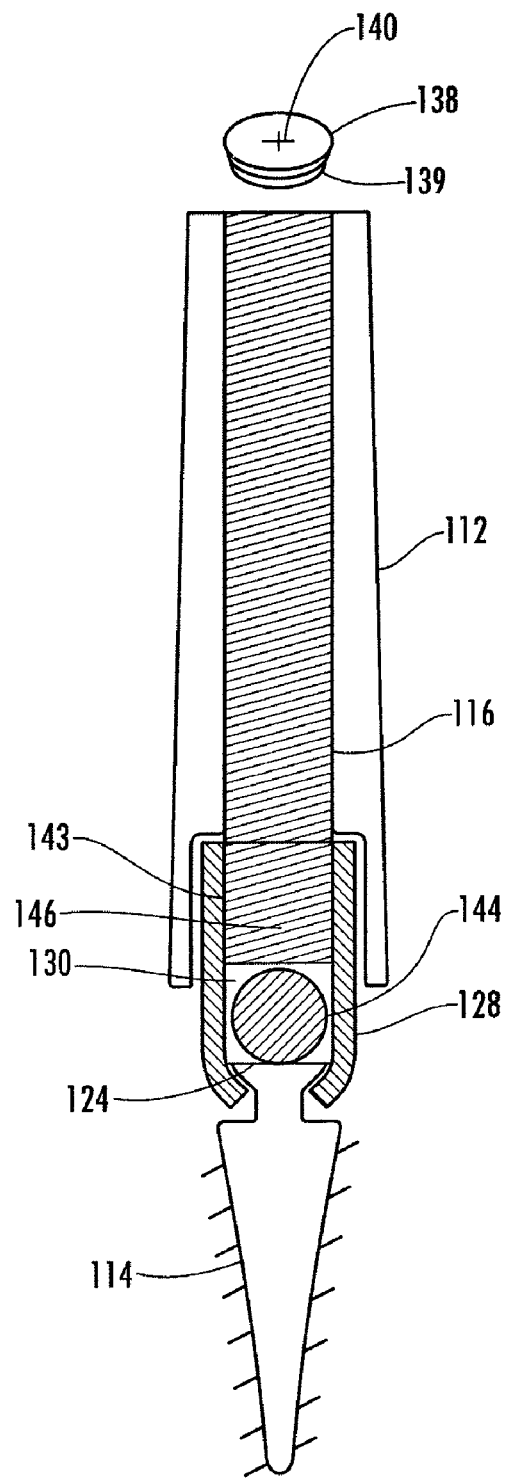
FIG. 14 is a sectional view of an extender and connector member each having internal threads that are indexed to one another so that that set screw may be threaded downwardly through the extender and the connector to secure the biocompatible material in place with respect to the fastener.

As shown in FIG. 14, the connector member 128 is constructed and arranged to form a passageway 130 designed to removably receive implants of various sizes. The connector 128 includes an opening 143 constructed and arranged to receive a set screw 138. The opening 143 includes threaded interior sidewalls 146 designed to mate with external threads 139 formed on the set screw 138. The extender 112 includes an inner cavity 114 that includes threads 116. The extender 112 is juxtaposed and mechanically engaged with the connector 128. The internal threads 116 of the extender 122 are indexed to the threads 146 in the connector 128. Thus, the set screw 138 is threadably lowered long the extender tube until it reaches the threads 146 formed within opening 143 located in the connector member 128. Since the threads 116 and 146 are indexed to one another the set screw 138 can continue to be threadably lowered into the connector 128. The provision of threads within the extender that are indexed to the threads of the connector is particularly useful when more than two screws are being connected with a rod or other biocompatible material. It has been found that when more than two screws are connected that the biocompatible material, such as a rod, tends to ride upward in chamber 143 of the third and subsequent connector 128. It is therefore an advantage to begin the threaded engagement of set screw 138 prior to reaching the upper end of connector 128. As the set screw is lowered the passageway 130 is narrowed until the exterior surfaces of the biocompatible device 144 (shown here as an interconnecting rod, see FIGS. 1-4) are sandwiched between the upper portion of the screw head 124 and the set screw 138. As with the head of the screw 114, there is a tool opening 140 configured to receive a driving tool. The tool is capable of driving the set screw 138 through the extender 112 and into the opening 143 to the desired position within the connector member 128.

Figure 15A:
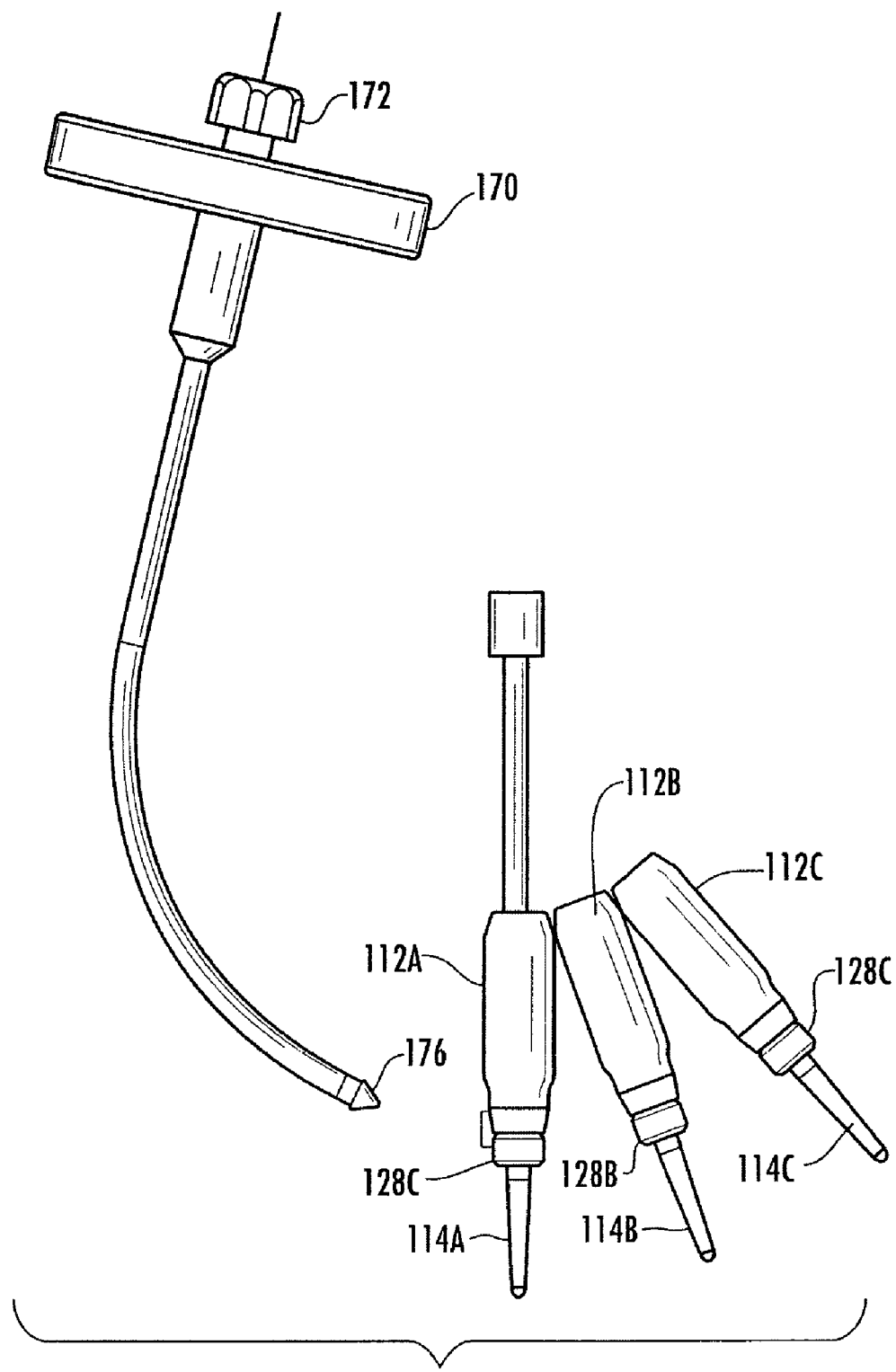
FIGS. 15A through 15O illustrate the various steps necessary for installation of the surgical implants where the connecting member between the fastening members is pulled into place.
Figure 15B:
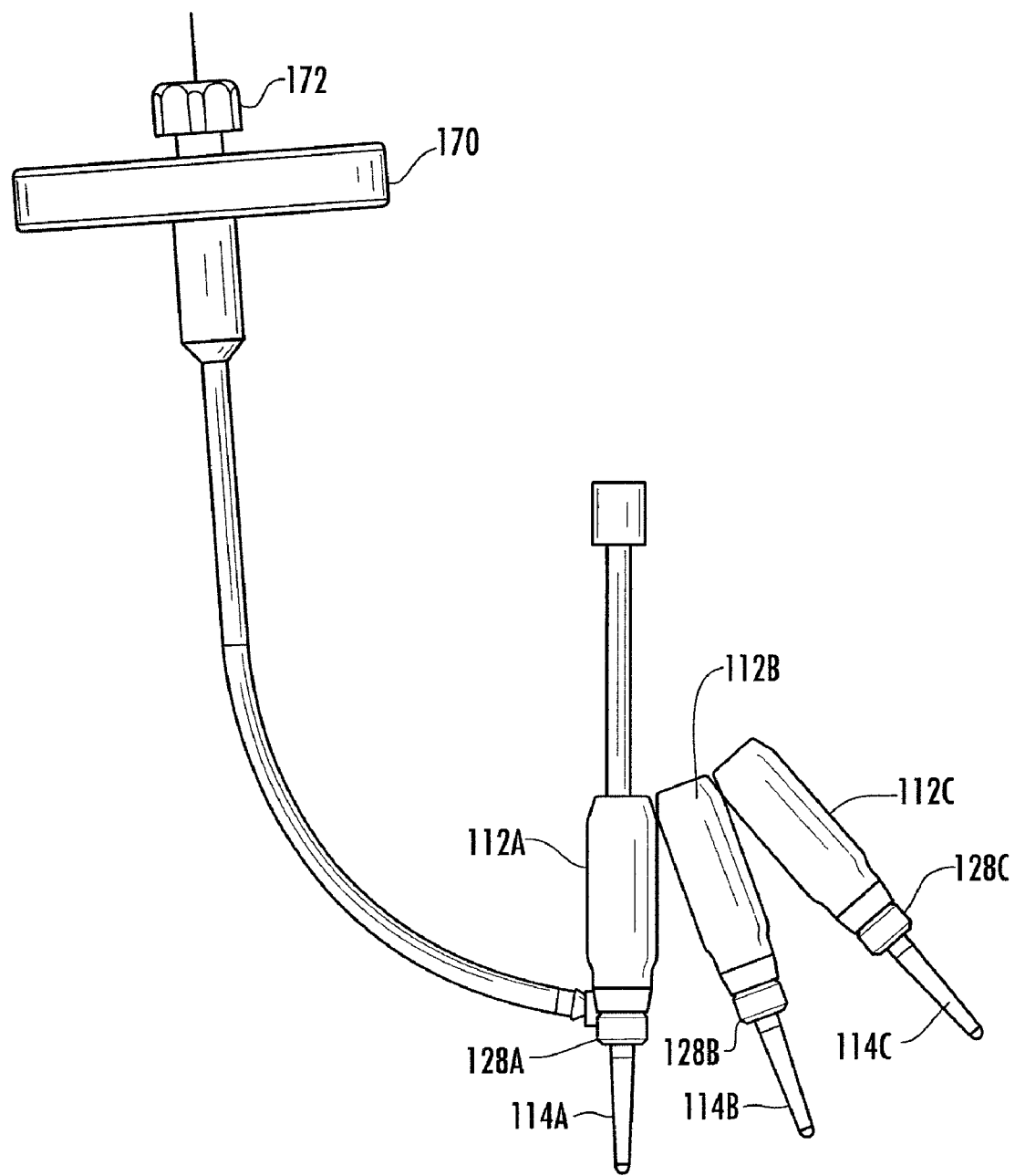
Figure 15C:
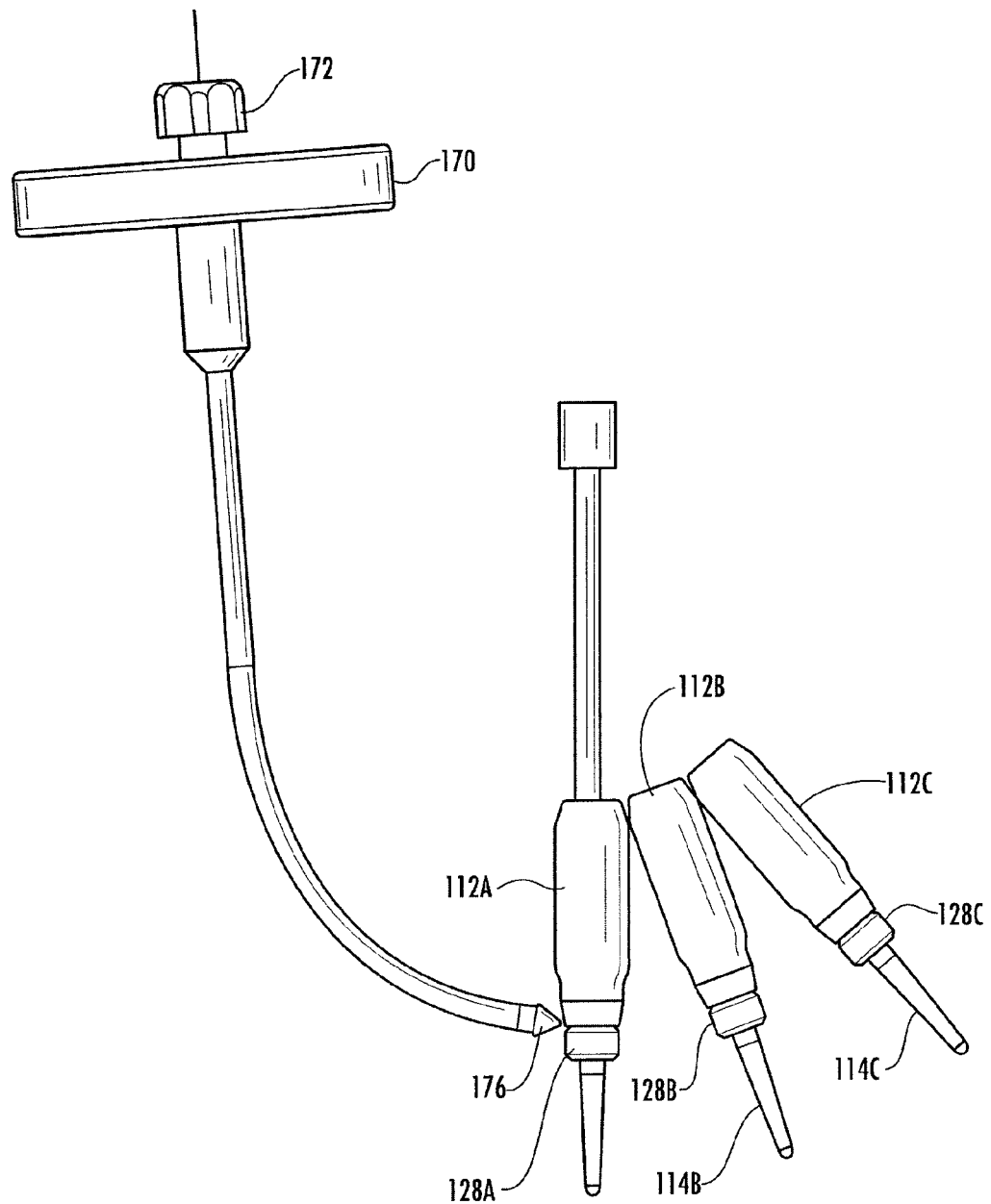
Figure 15D:
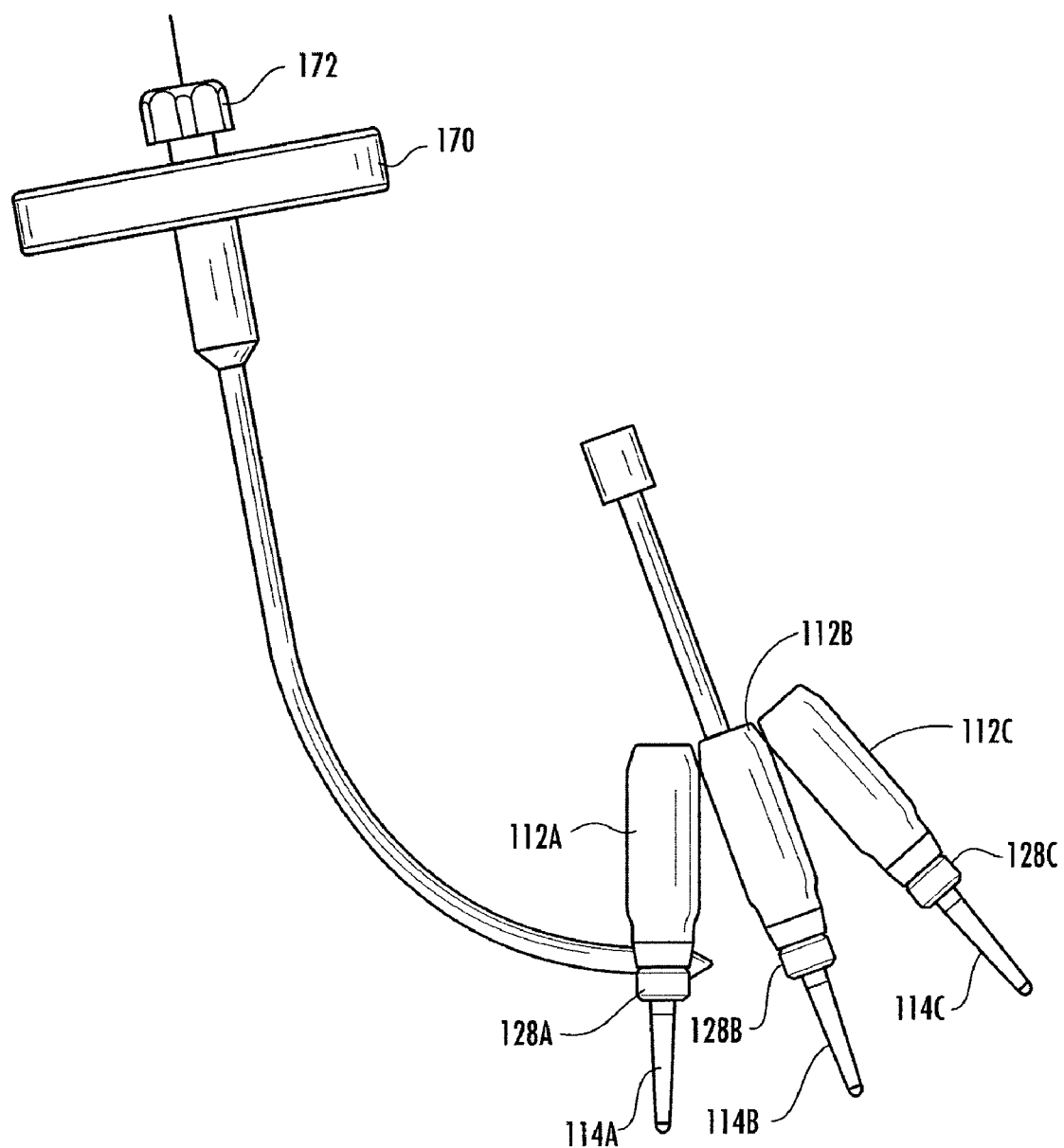
Figure 15E:
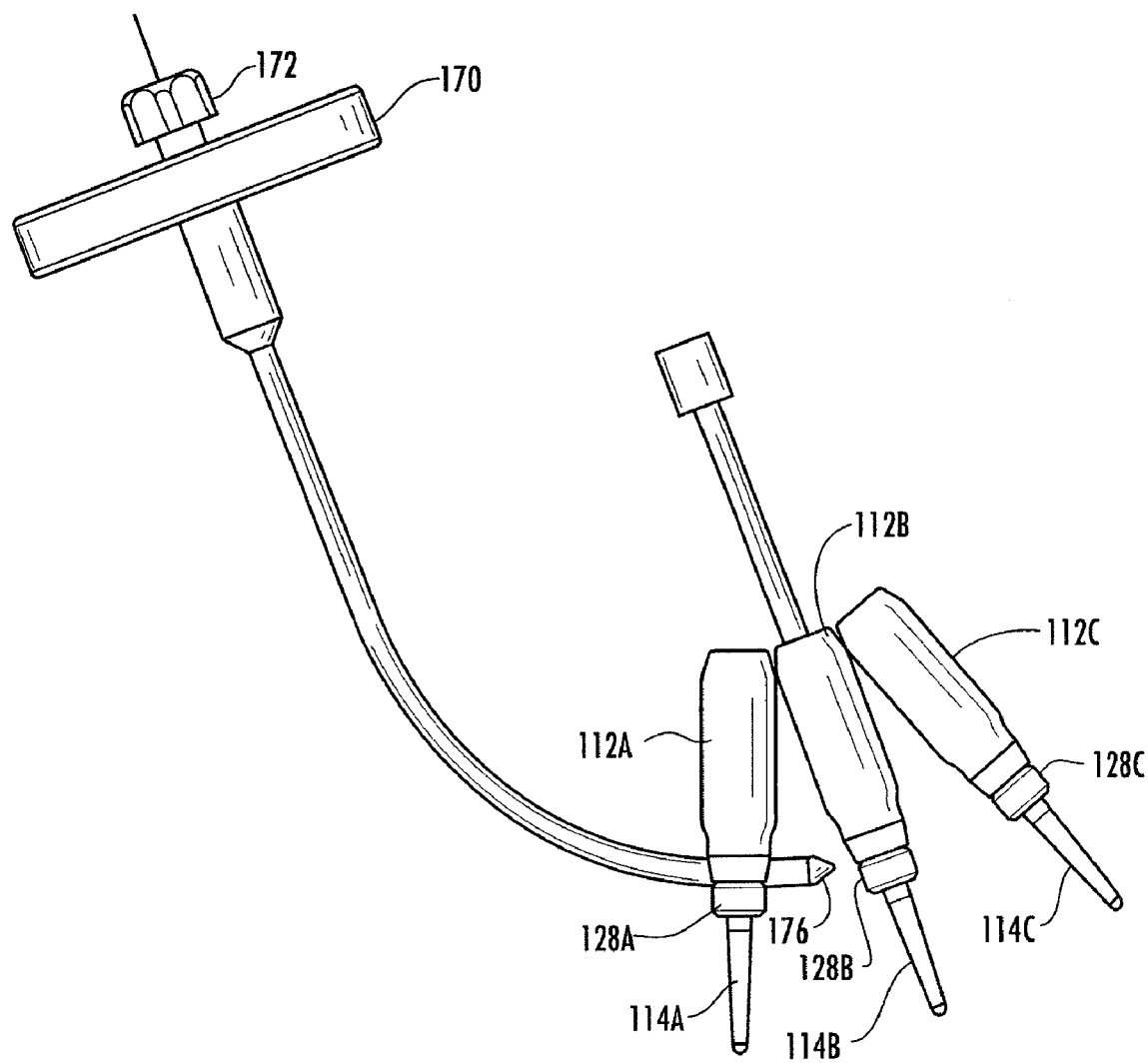
Figure 15F:
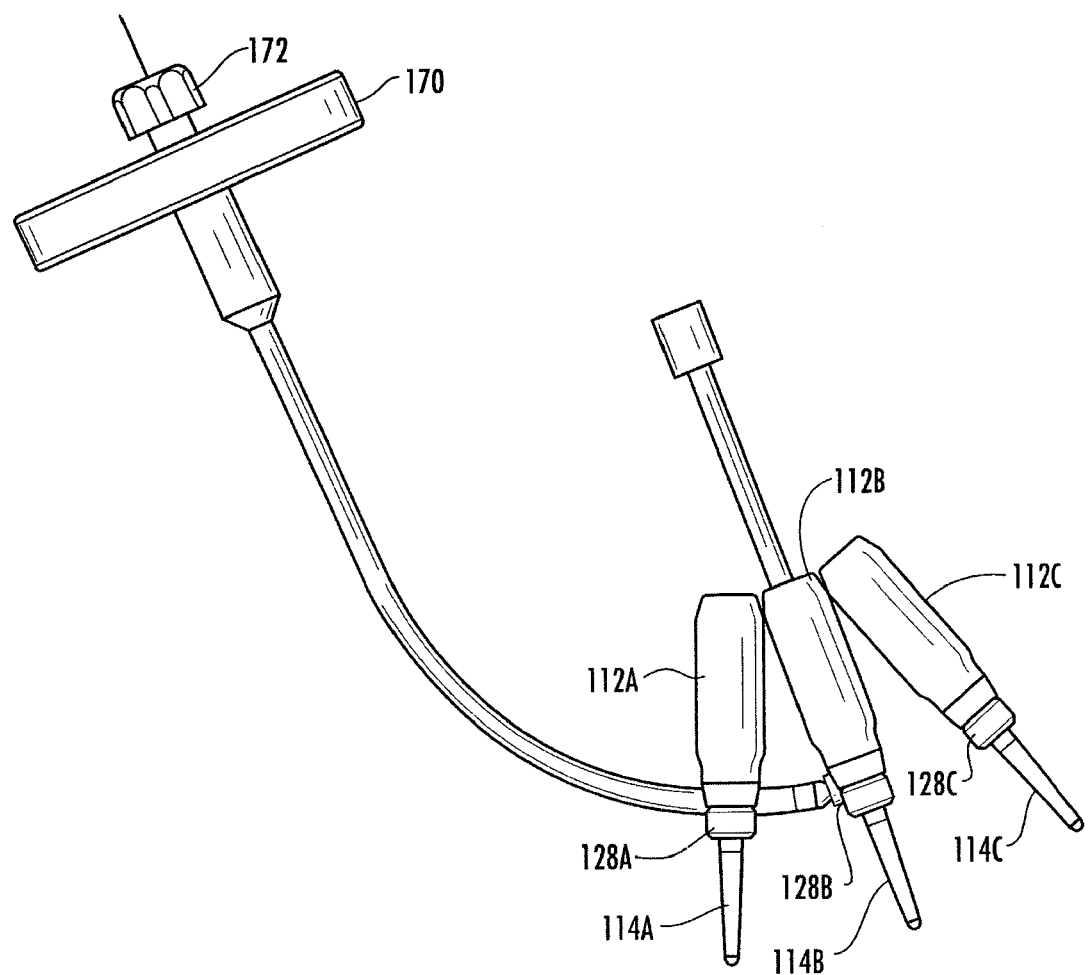
Figure 15G:
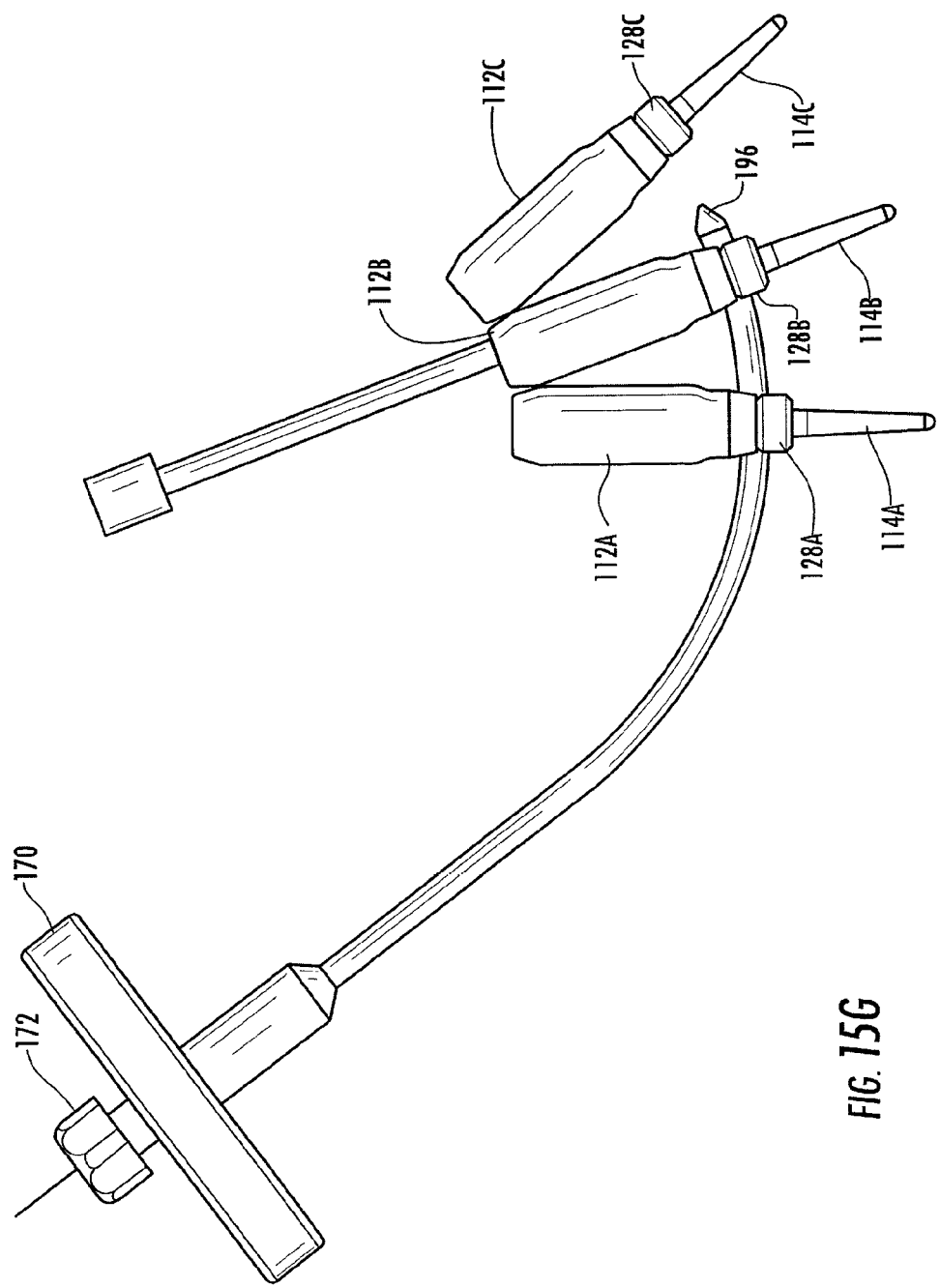
Figure 15H:
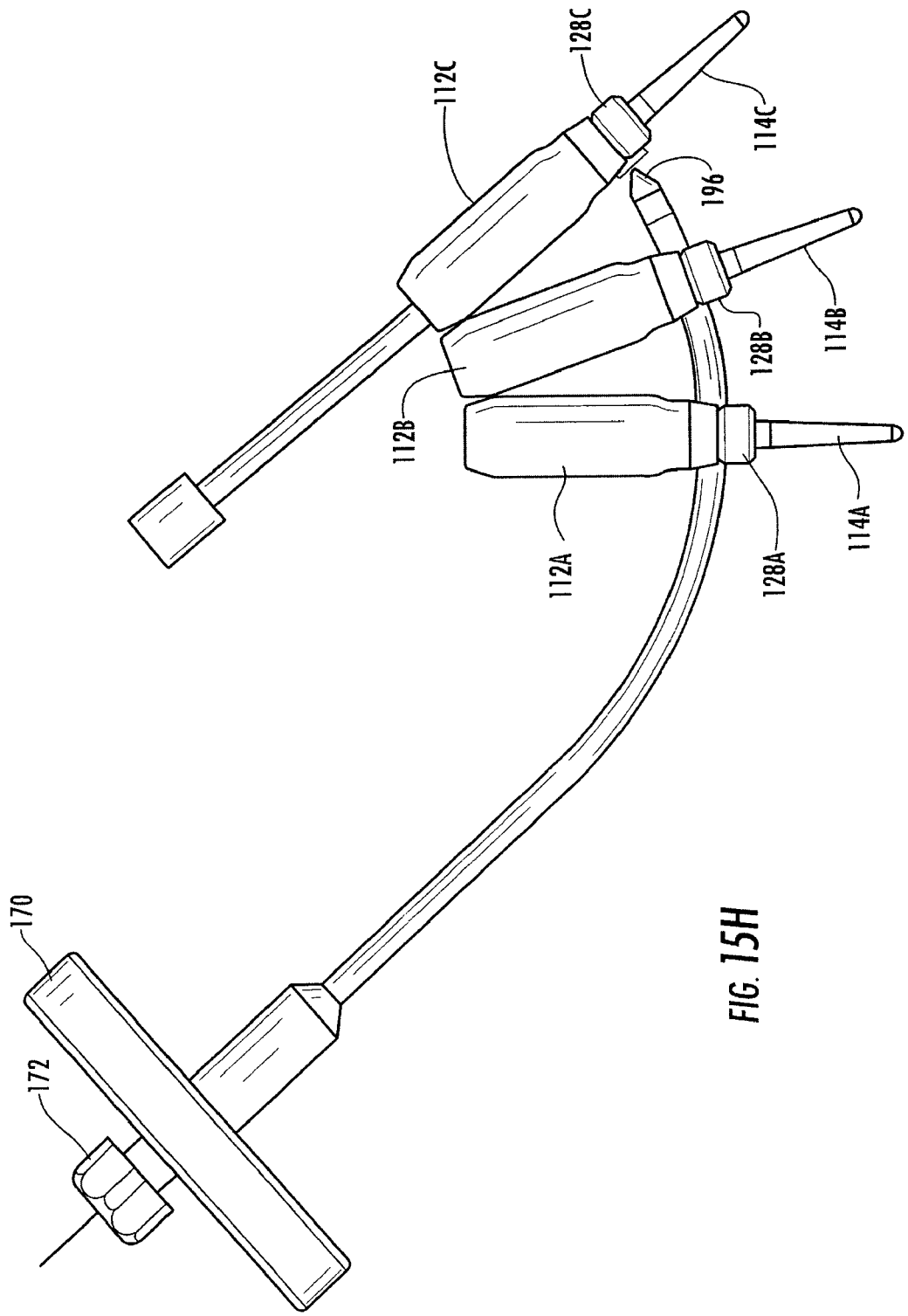
Figure 15I:
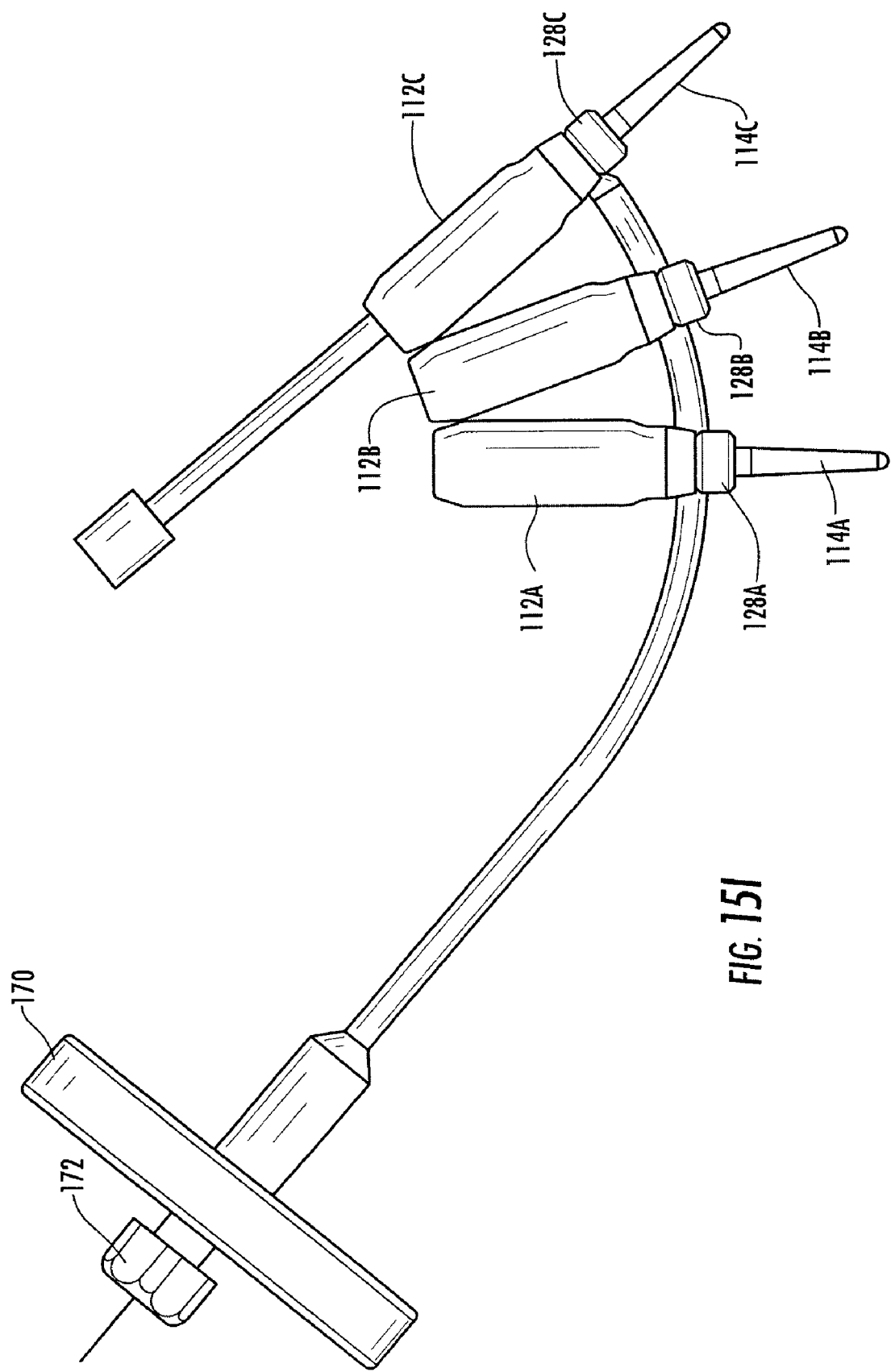
Figure 15J:
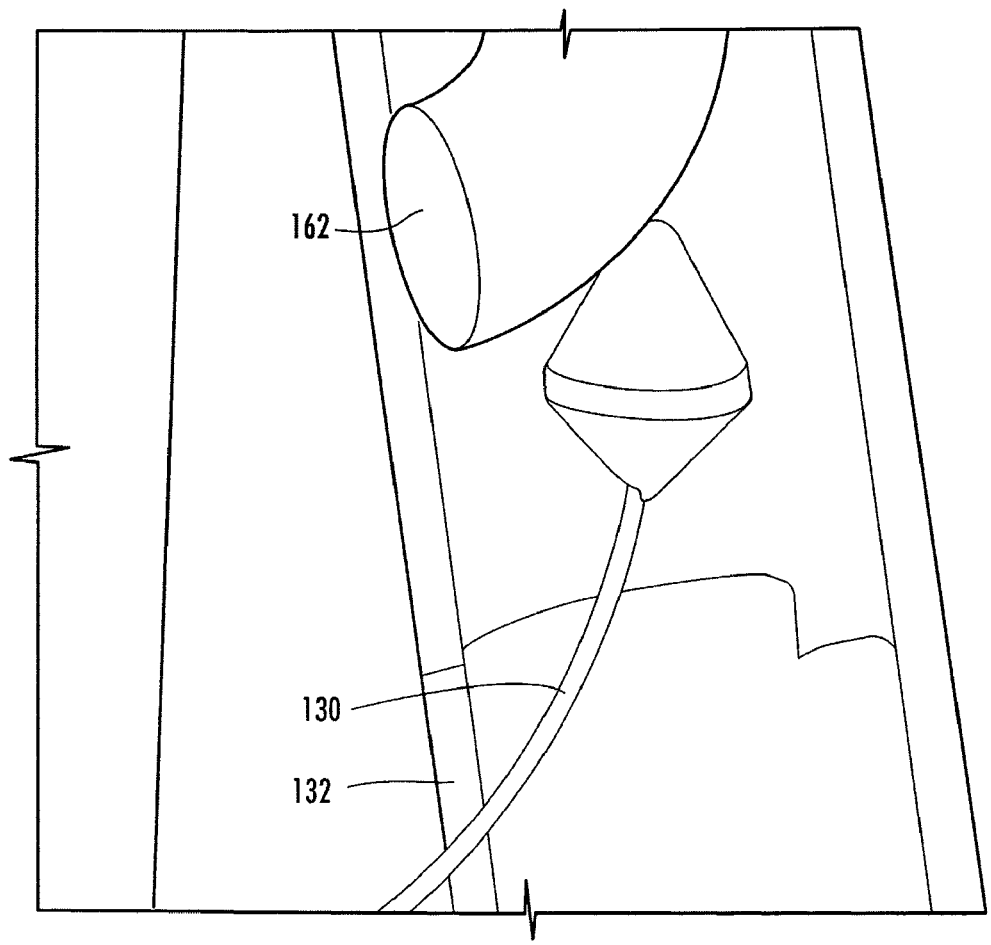
Figure 15K:
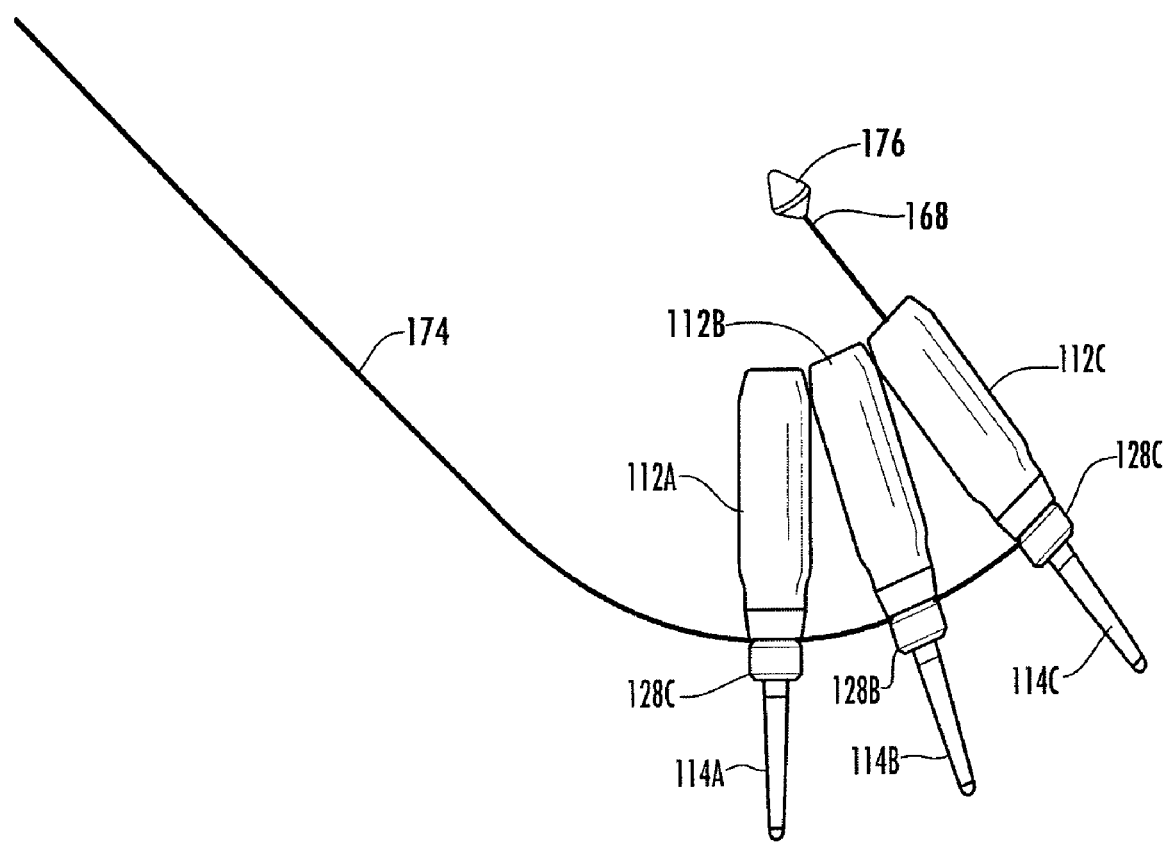
Figure 15L:
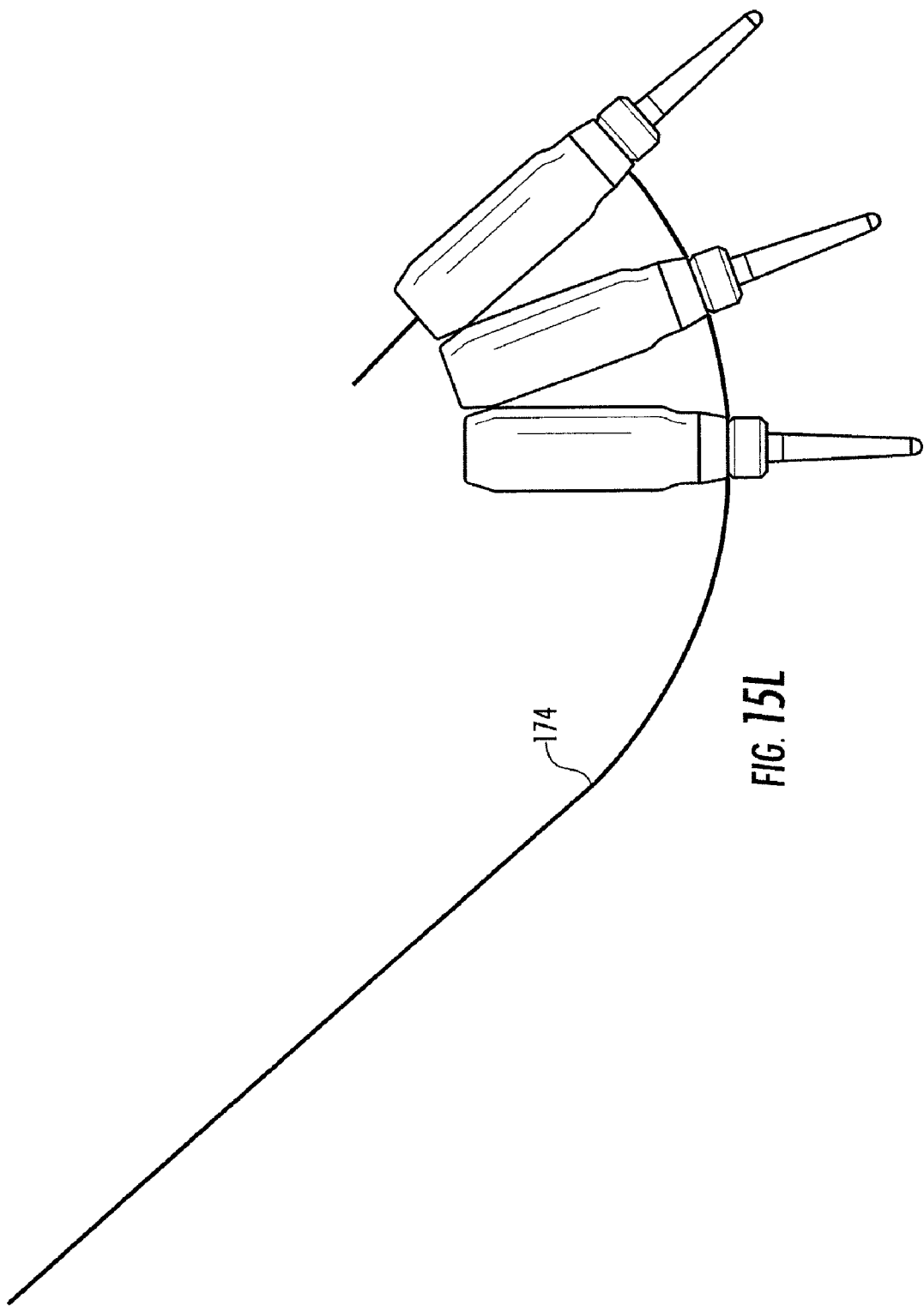
Figure 15M:
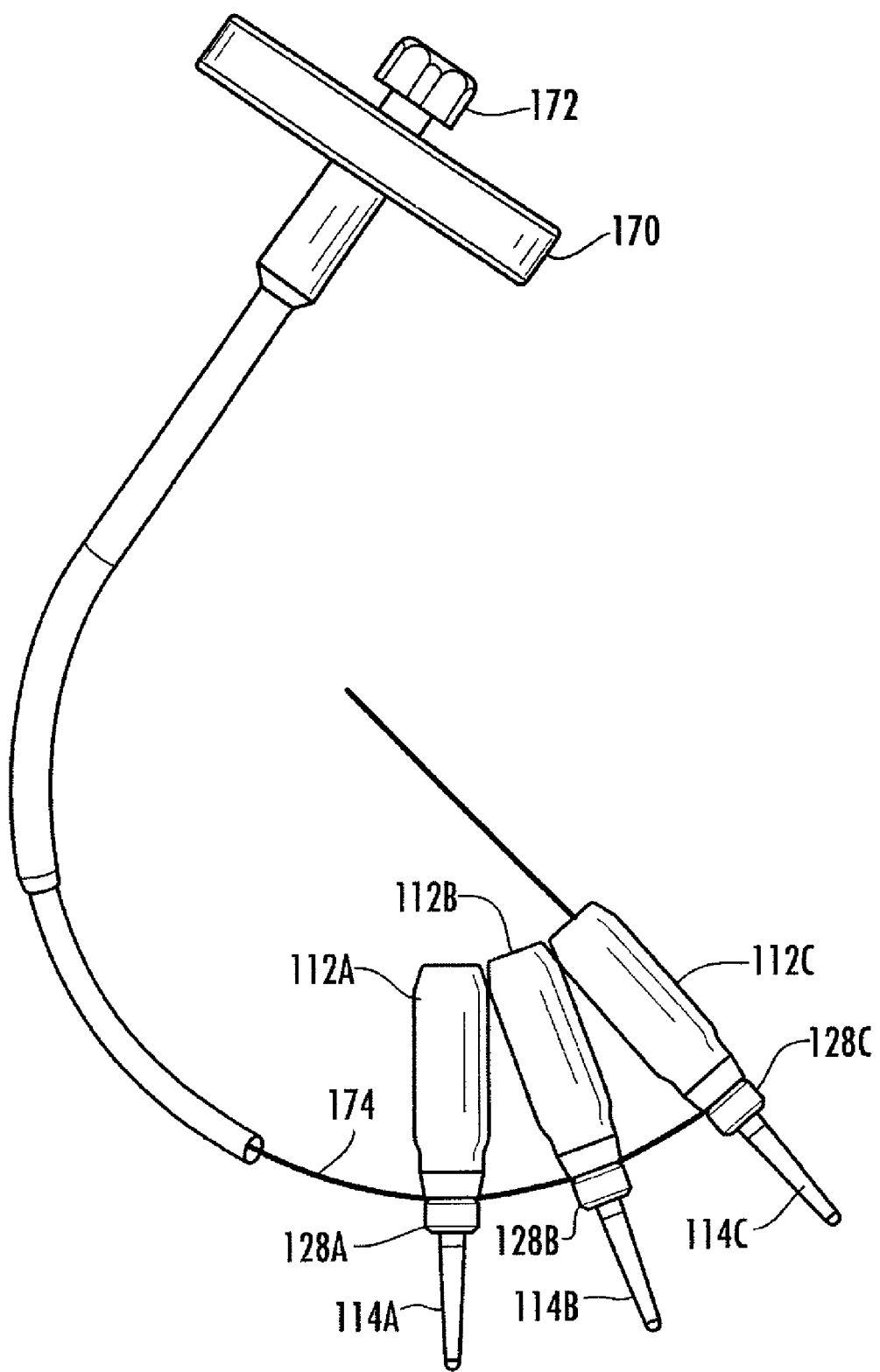
Figure 15N:
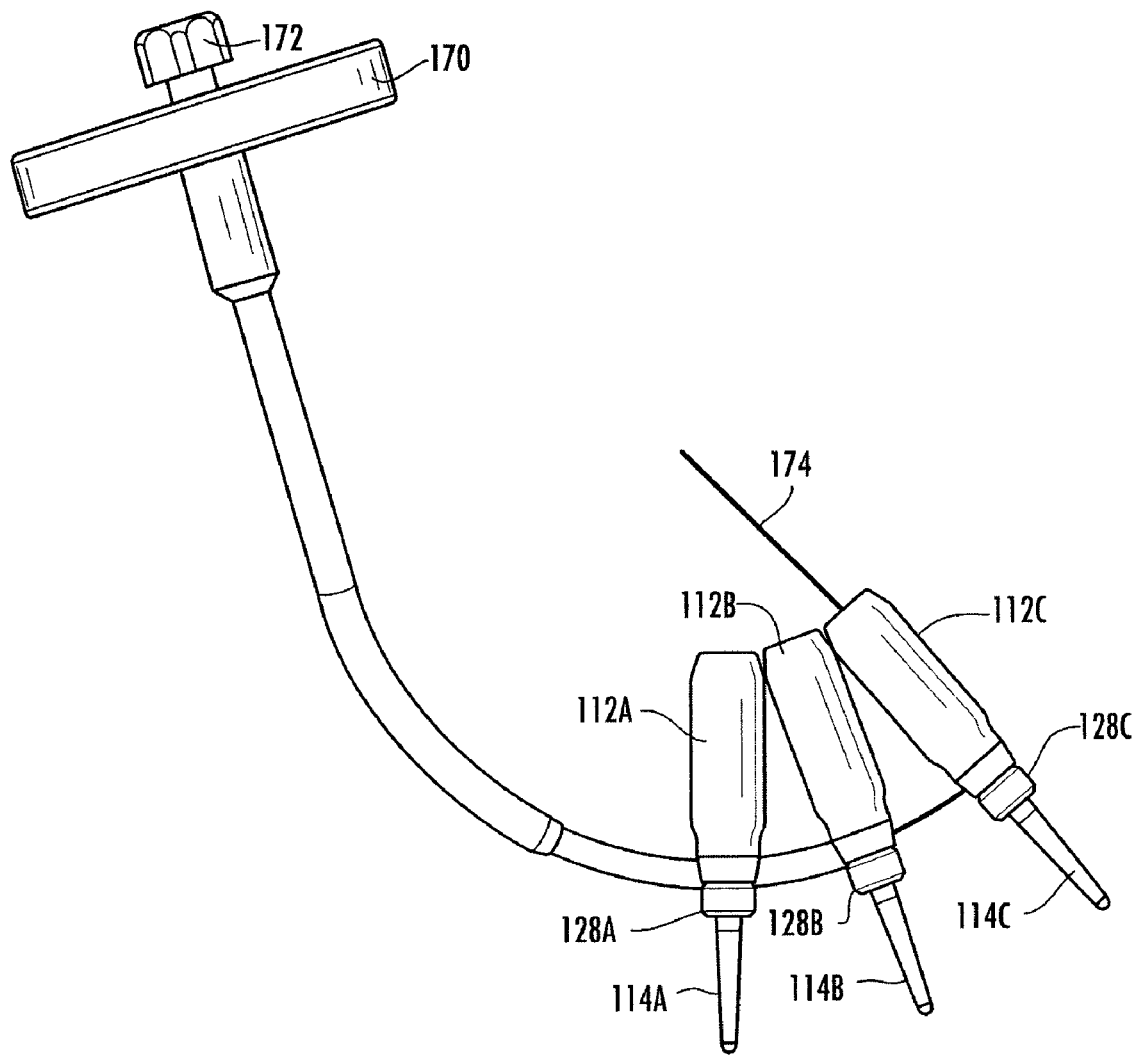
Figure 150:
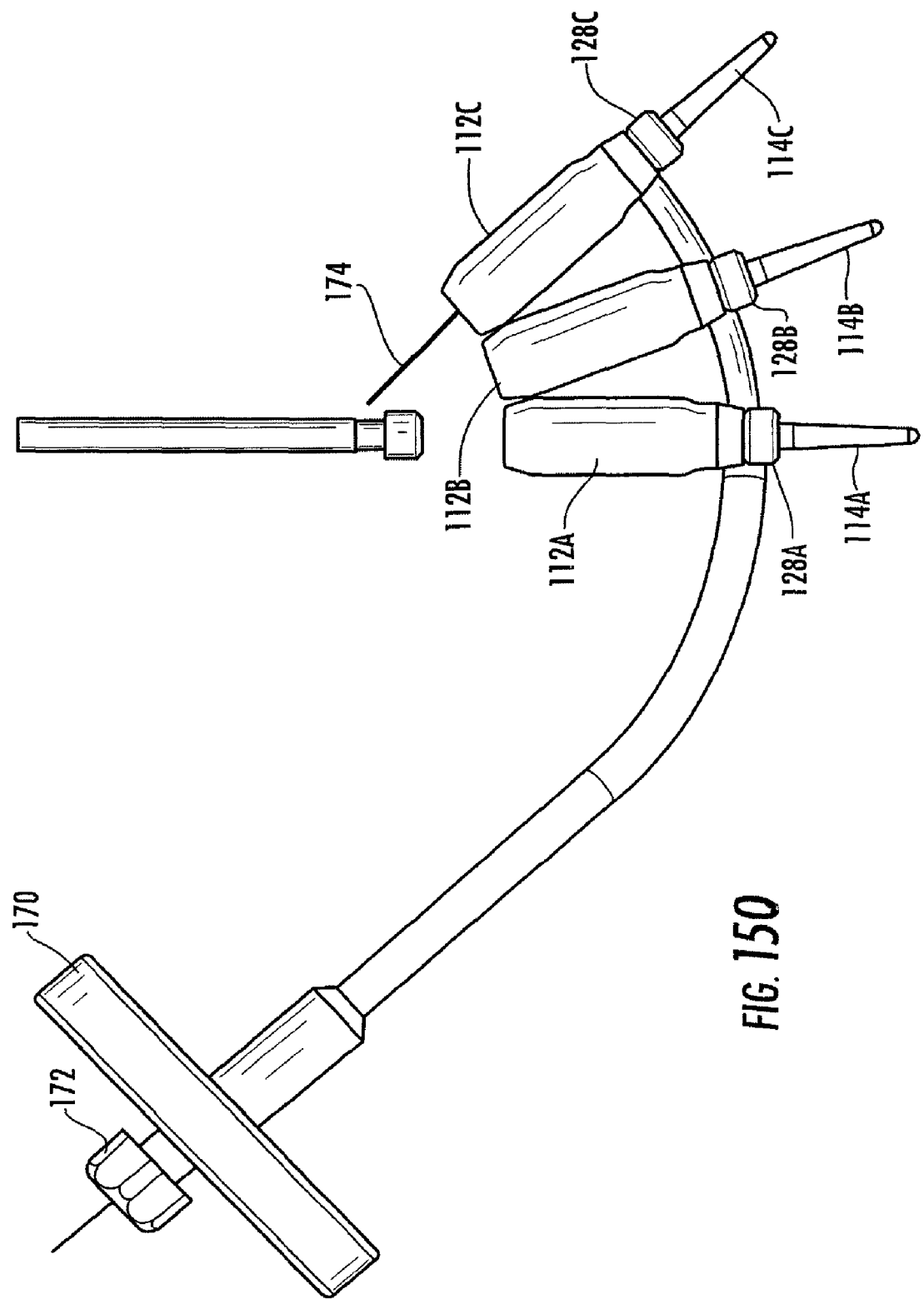

FIGS. 15A through 15O illustrate the various steps necessary for installation of the surgical implants where the connecting member between the fastening members is pulled into place. FIG. 15A shows a freehand inserter 170 that is introduced into a caudal or cephlad incision. The first fastening member, screw 114A, is approached under fluro, where the surgeon will feel for positive resistance. As the target 176, which is carried on the leading end of the freehand inserter 170, approaches the magnetic catcher 162 the surgeon will feel for conformation of positive engagement by repeated tactile "snap" or "click", as shown in FIG. 15B. With the target 176 in alignment with connector passageway 130 and extender passageway 132 the catcher magnet 162 and wand 160 are moved upwards within the extender 112A, as illustrated in FIG. 15C. FIG. 15D depicts the freehand guide 170 moving forward towards the second fastener 114B with the catcher magnet 162 removed from the first extender tube 112A and placed in the second extender tube 112B. FIGS. 15E, F and G illustrate the process for the second fastener 114B. The process is the same as it was for the first fastener except much easier because of the close proximity between the first and second fastener. The freehand inserter 170 then advances the tip 176 towards the magnet catcher 162 positioned adjacent the third fastener 114C, as shown in FIGS. 15H. The knob 172 on freehand inserter 170 is then loosened which releases tether means 174 that is attached to the magnetic tip 176. The magnetic tip 176 then follows the magnetic catcher as it is withdrawn from the third and last extender tube 112C as shown in FIGS. 15I and 15J. As shown in FIG. 15K, the magnetic tip 176 follows the magnetic catcher out of extender 112C and the freehand guide is removed. At this point the tether means enters the initial incision and all three screw connectors, 128A, 128B and 128C, and exits out the last extender 112C, as shown in FIGS. 15L, 15M and 15N. A soft or solid rod can be pulled into place by positioning the rod with the freehand inserter 170 and pulling the tether means 174 through all three screw connectors 128A, 128B and 128C. The rod is released from the wire 174 using a break away connection 168(see FIGS. 15K and 15O).

Figure 16A:
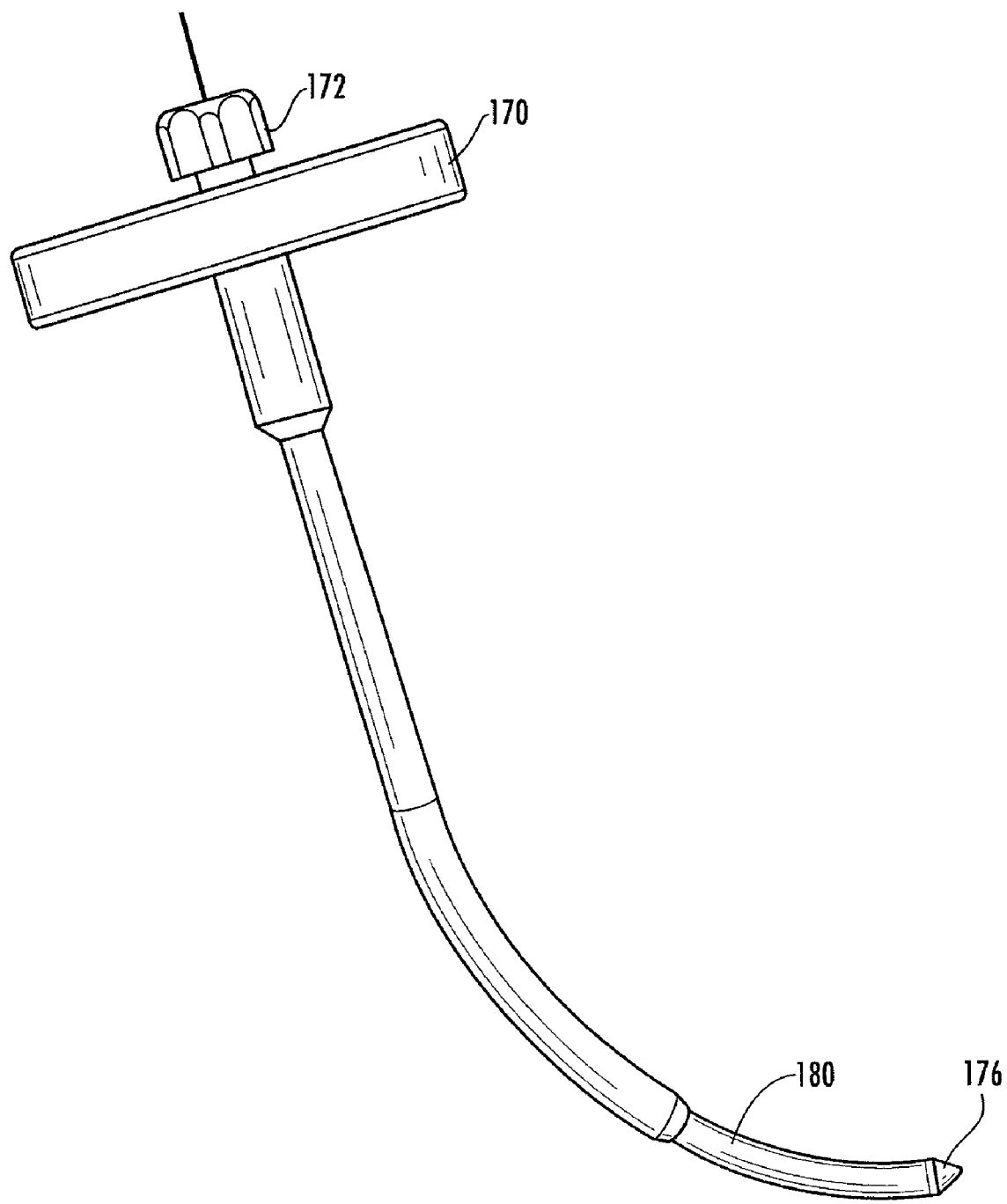
Figure 16B:
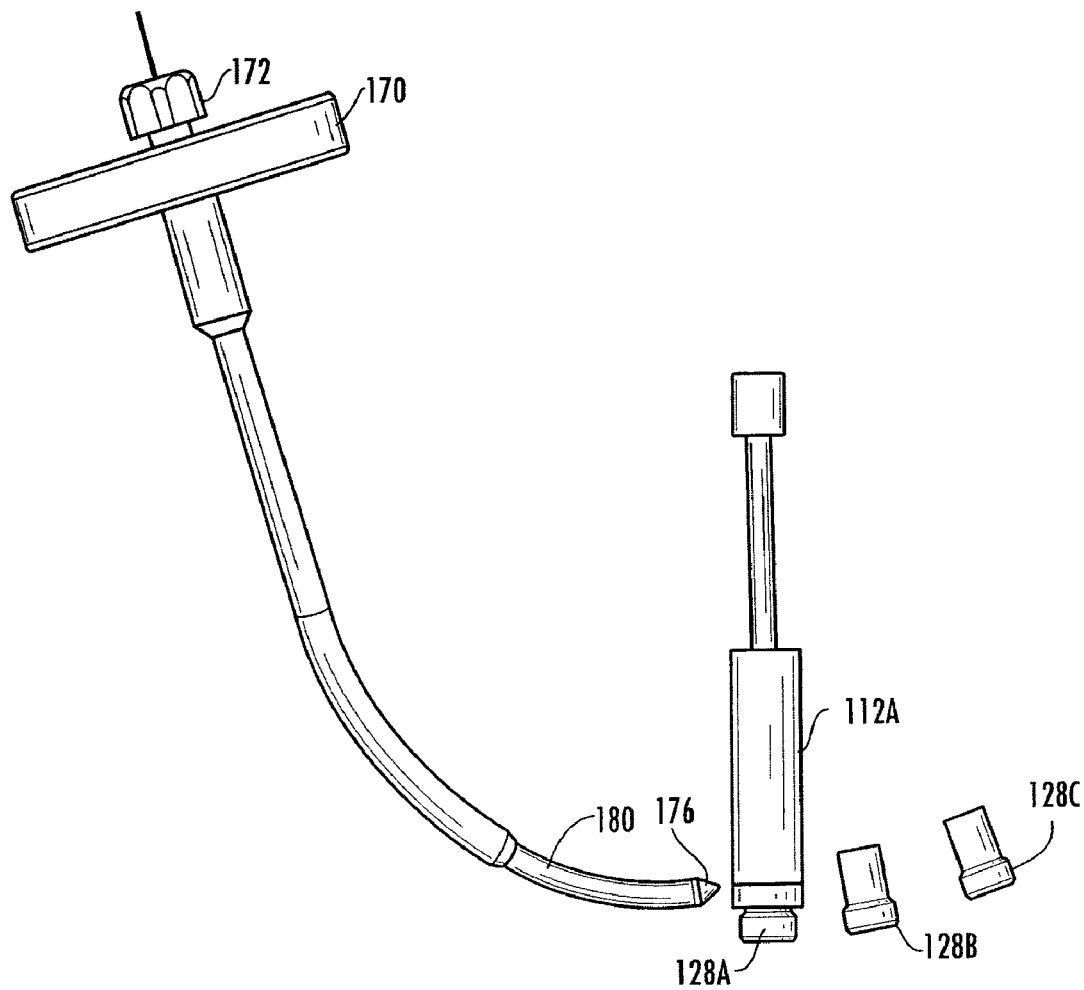
Figure 16C:
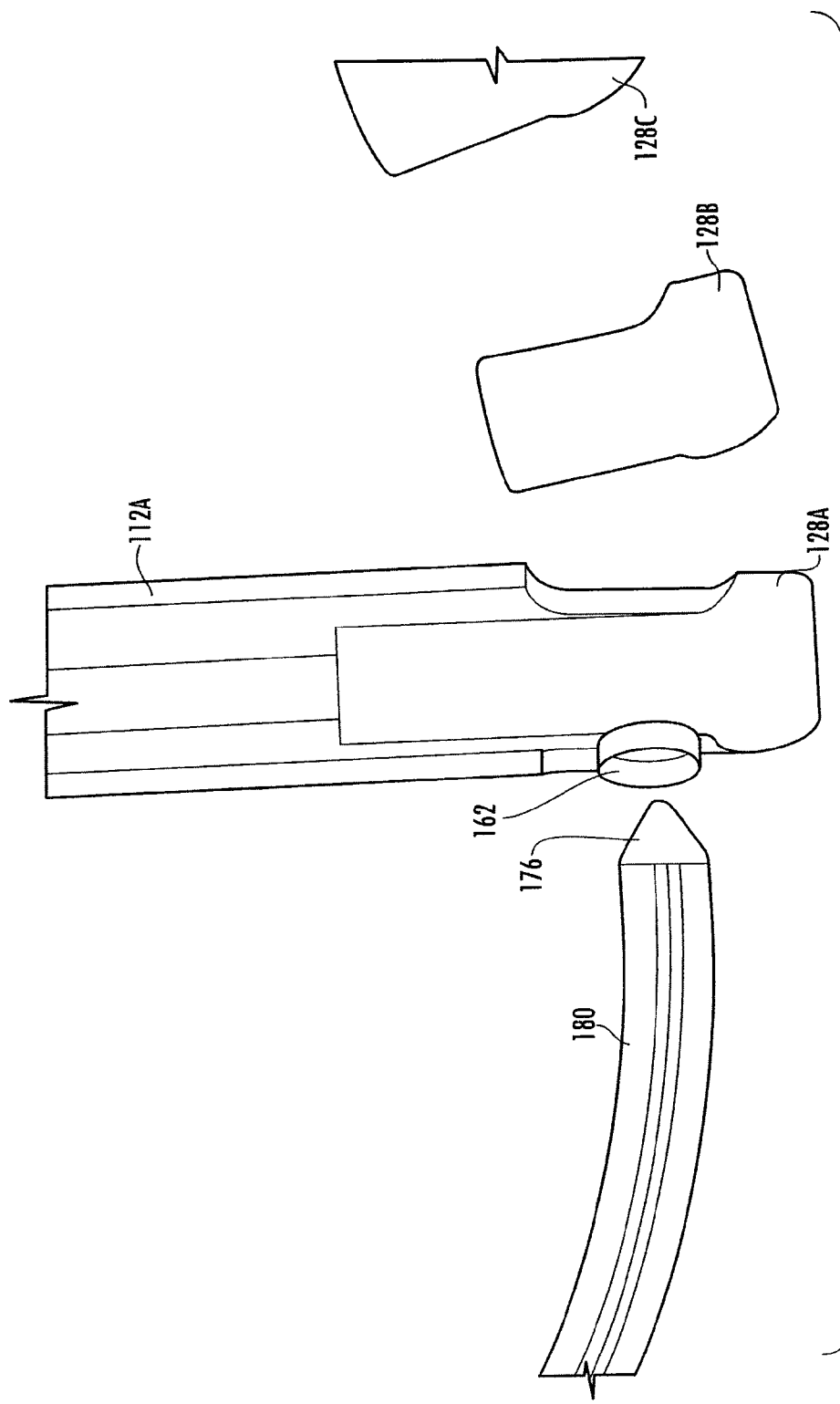
Figure 16E:
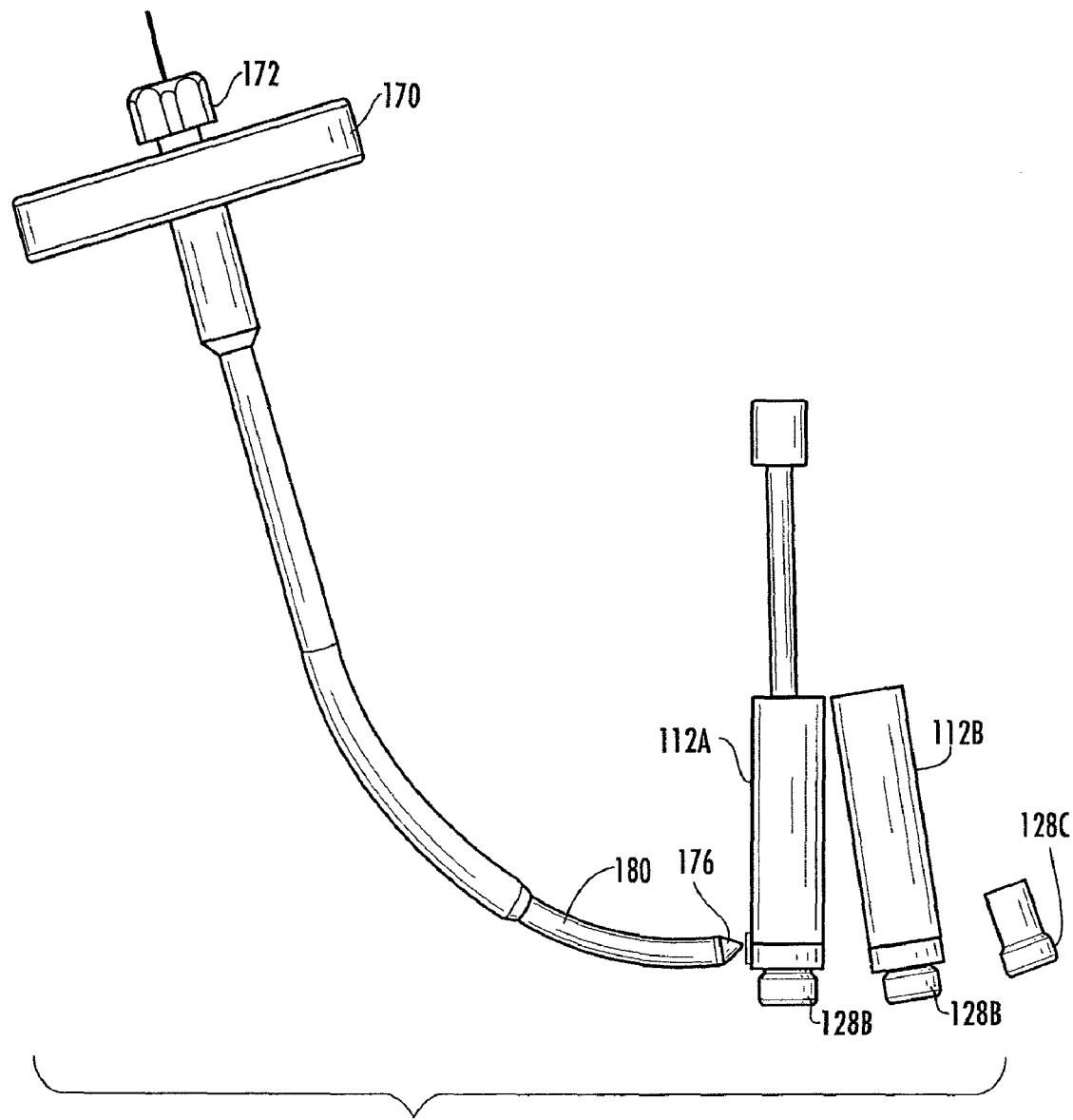
Figure 16F:
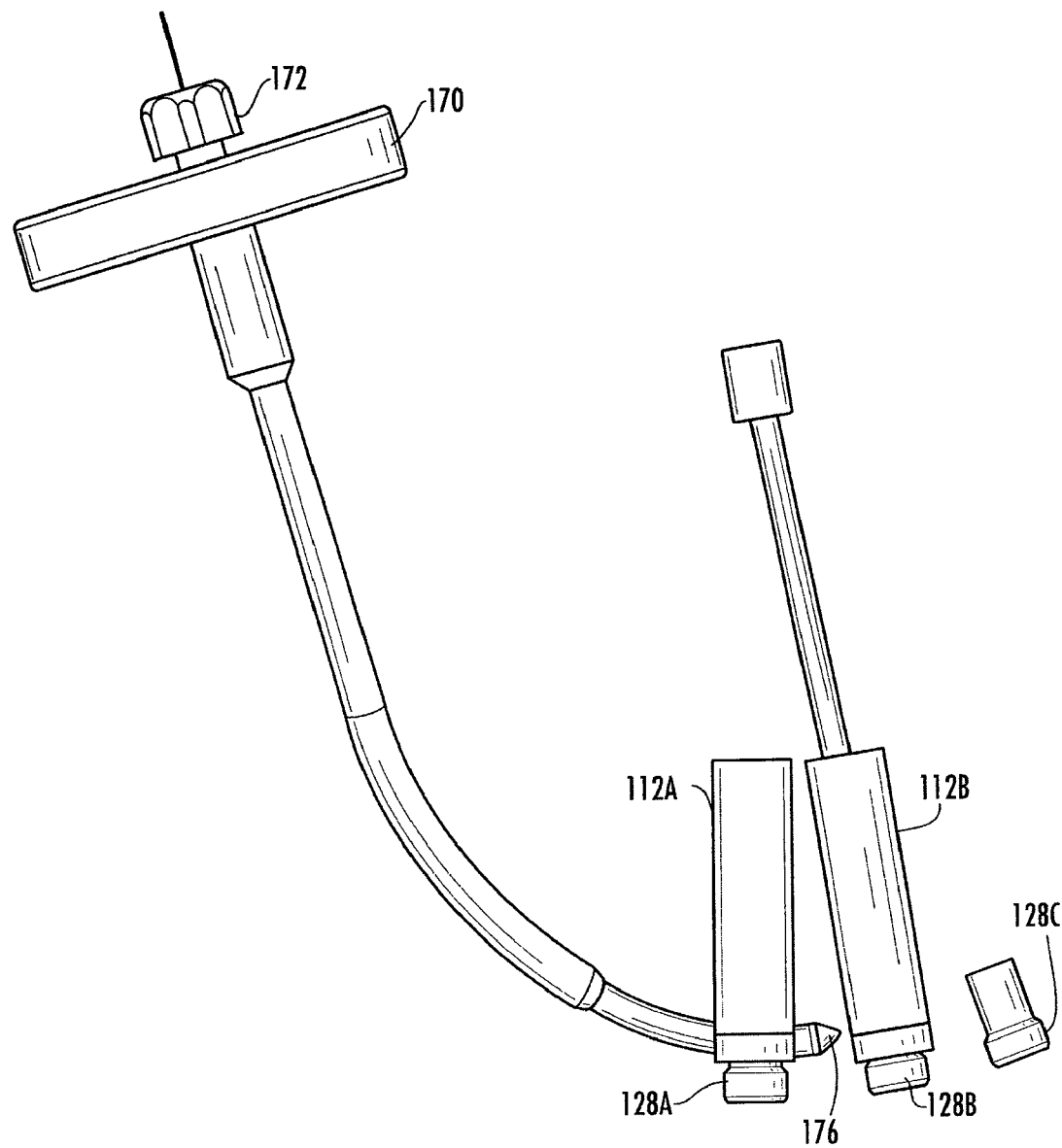
Figure 16G:
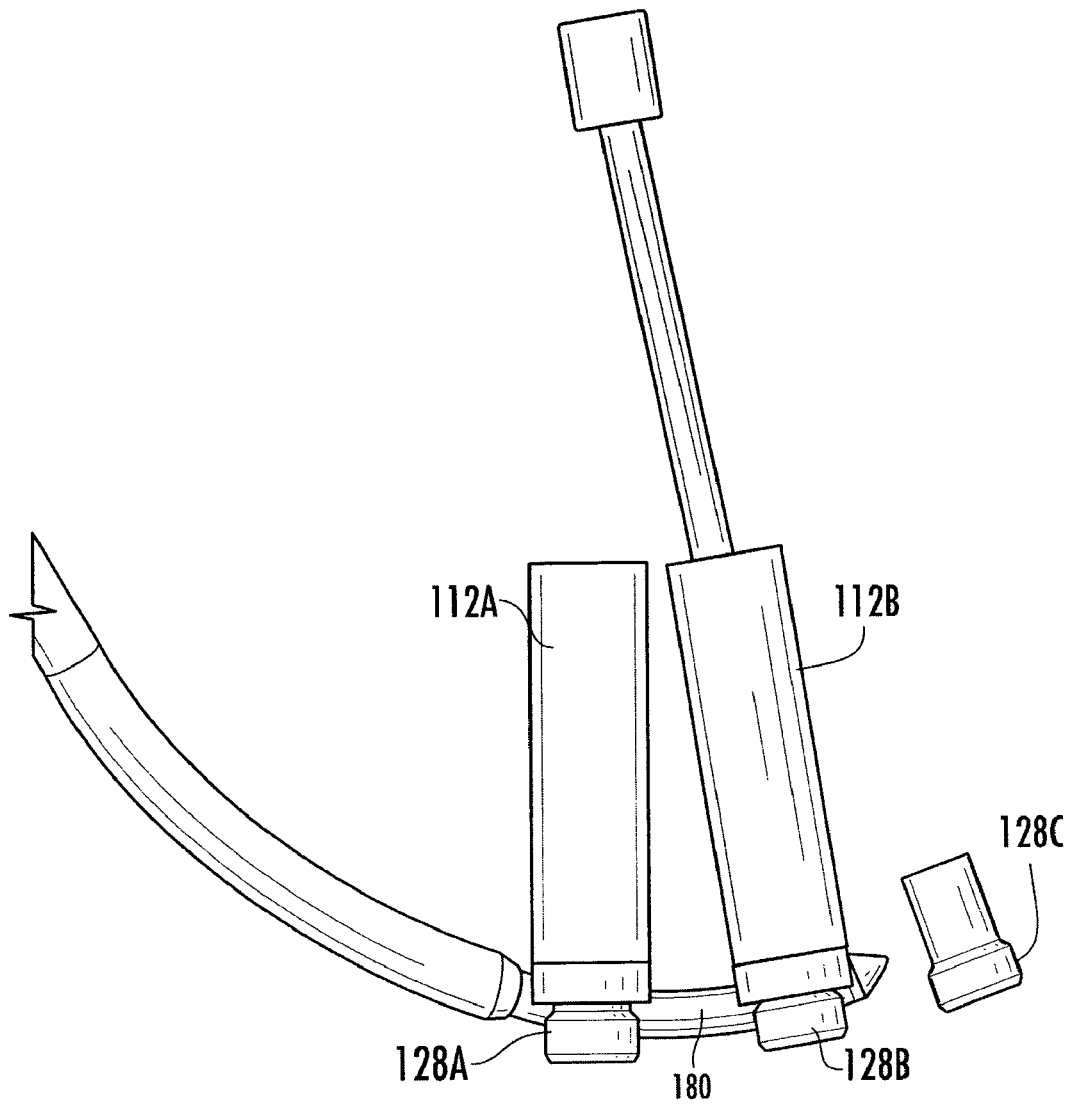
Figure 16H:
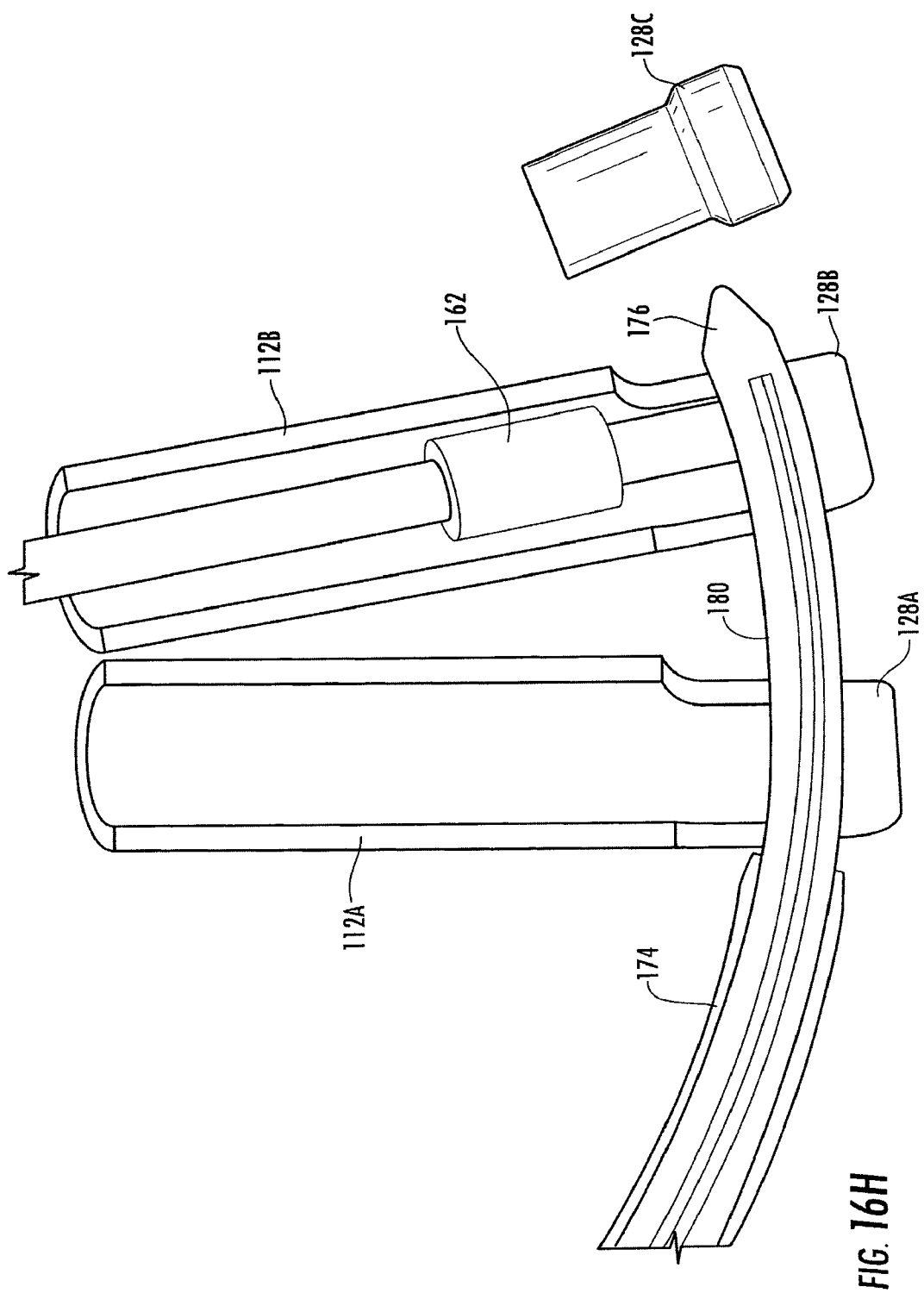
Figure 161:
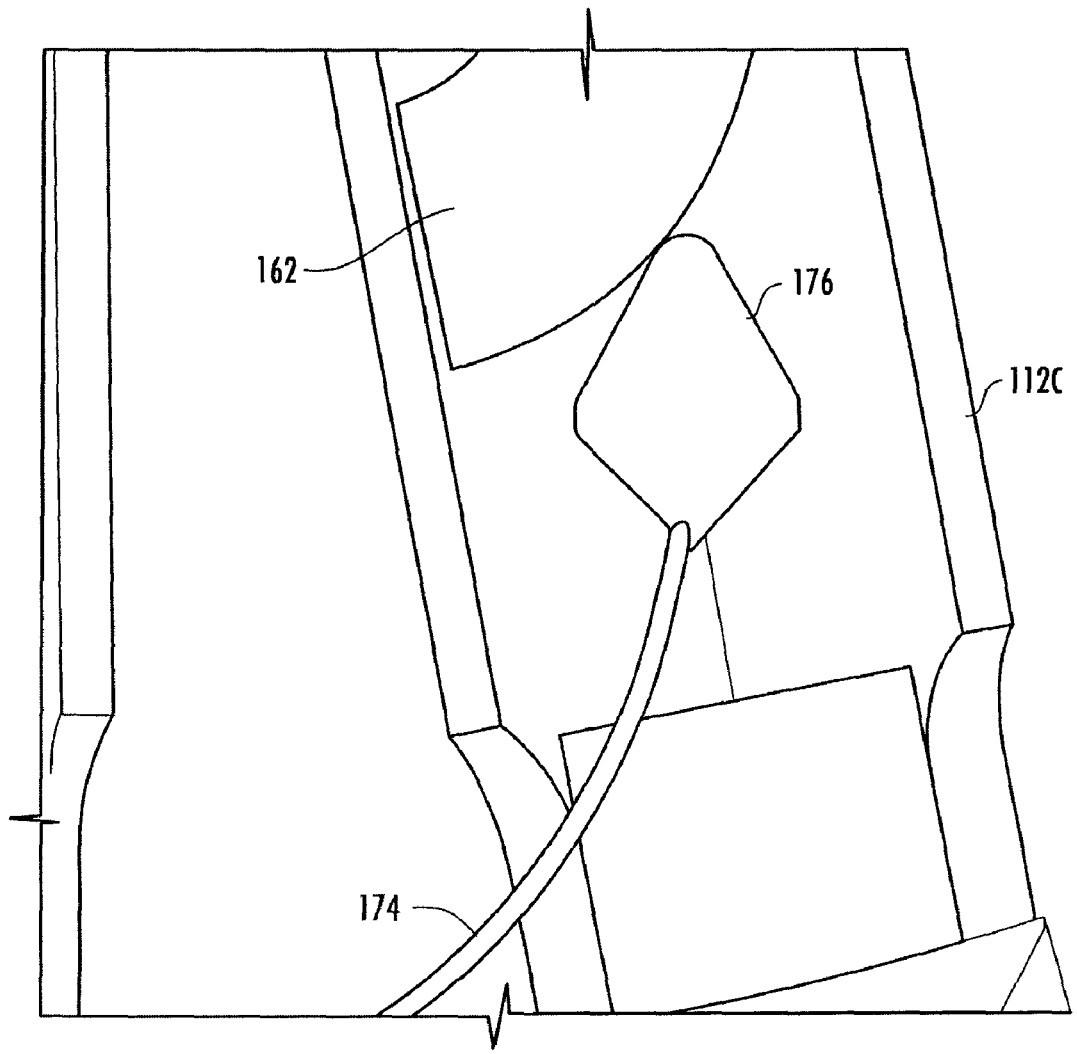
Figure 16J:
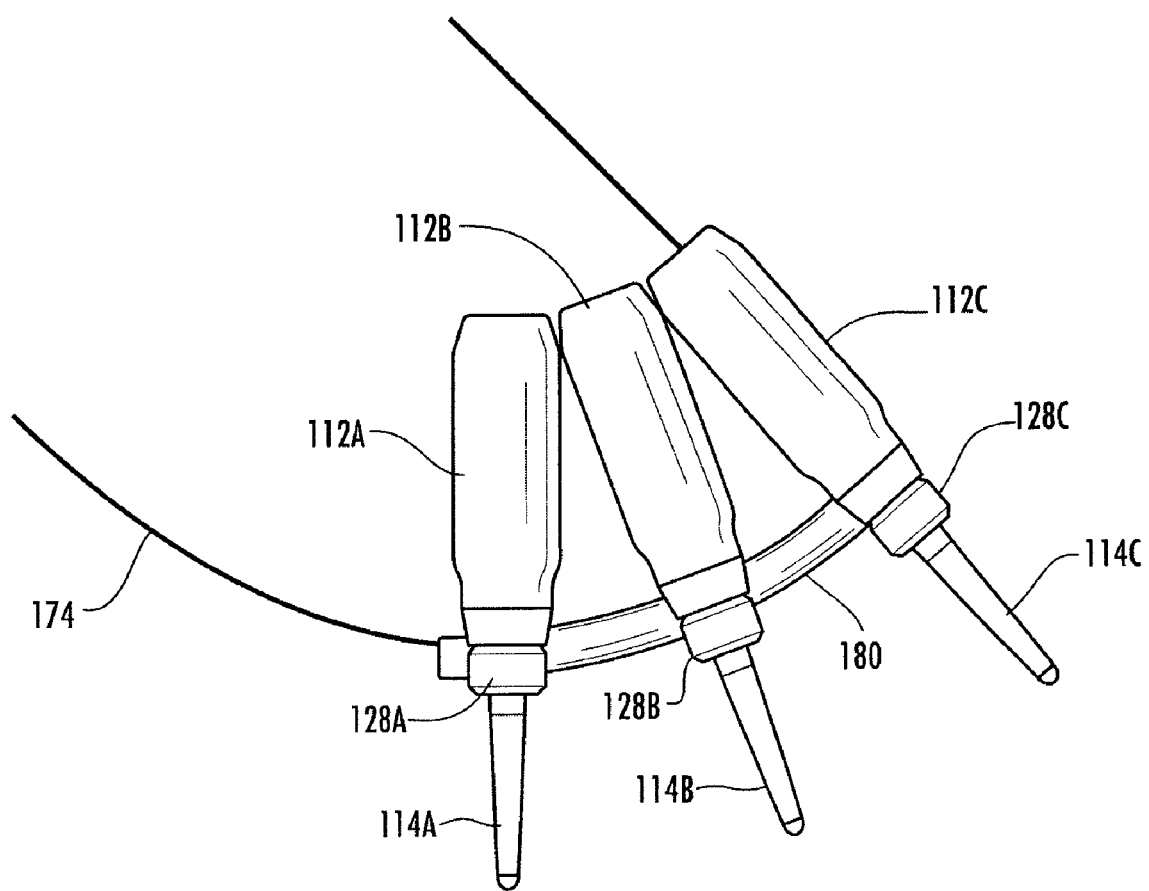
Figure 16K:
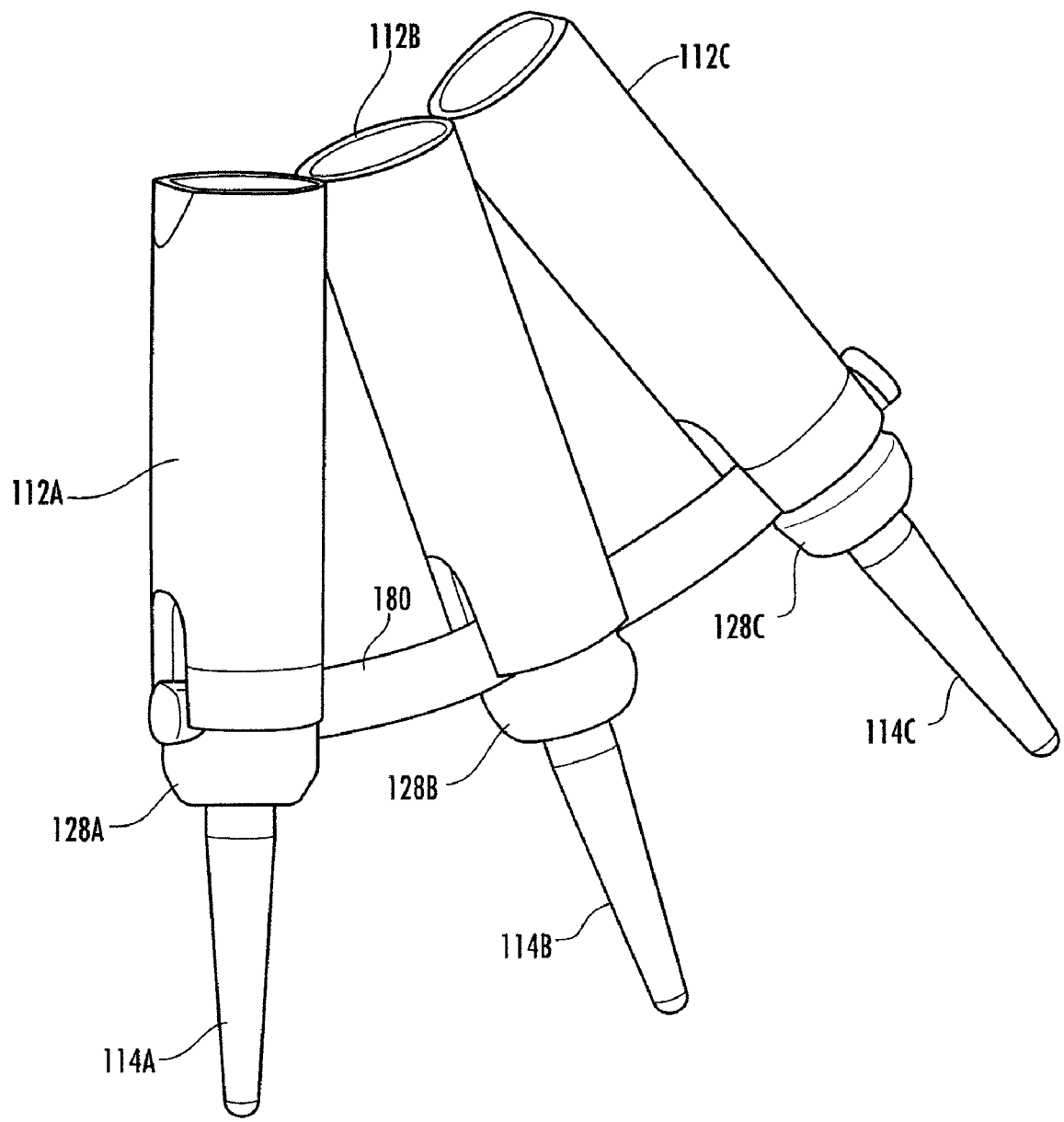

FIGS. 16A through 16L illustrate the various steps the various steps necessary for installation of the surgical implants where the connecting member between the fastening members is pushed into place. FIG. 16A shows an arrangement which uses a cannulated rod 180 which is assembled as part of the freehand guide 170 utilizing tether means 174, target member 176, and the tether means securing knob 172 on freehand guide 170. In this arrangement the cannulated solid rod 180 carries the targeting member 176 at its leading end and the cannulated rod is in turn positioned on the leading end of the freehand inserter 170. The first fastening member, screw 114A, is approached under fluro, where the surgeon will feel for positive resistance. As the target 176, which is carried on the leading end of the cannulated rod 180, approaches the magnetic catcher 162 the surgeon will feel for conformation of positive engagement by repeated tactile "snap" or "click", as shown in FIGS. 16B, 16C, 16D and 16E. With the target 176 in alignment with connector passageway 130 and extender passageway 132 the catcher magnet 162 and wand 160 are moved upwards within the extender 112A. FIG. 16F depicts the freehand guide 170, cannulated solid rod 180 and magnetic tip 176 pushed forward towards the second fastener 114B with the catcher magnet 162 removed from the first extender tube 112A and placed in the second extender tube 112B. FIGS. 16F, and 16G illustrate the process for the second fastener 114B. The process is the same as it was for the first fastener except much easier because of the close proximity between the first and second fastener. The freehand inserter 170 then advances the cannulated rod 180 and the tip 176 towards the magnet catcher 162 positioned adjacent the third fastener 114C, as shown in FIG. 16H. The knob 172 on freehand inserter 170 is then loosened which releases tether means 174 that is attached to the magnetic tip 176. The magnetic tip 176 then follows the magnetic catcher as it is withdrawn from the third and last extender and the freehand guide is removed, as shown in FIG. 16I. The freehand guide 170 then pushes the cannulated rod into position on the third fastener 128C and the magnetic target is released from the tether means 174 by a breakaway connector. The tether means 174 is then removed from the body. The installed cannulated rod 180 is shown in an assembled position in FIGS. 16J, 16K and 16L.

Figure 17A:
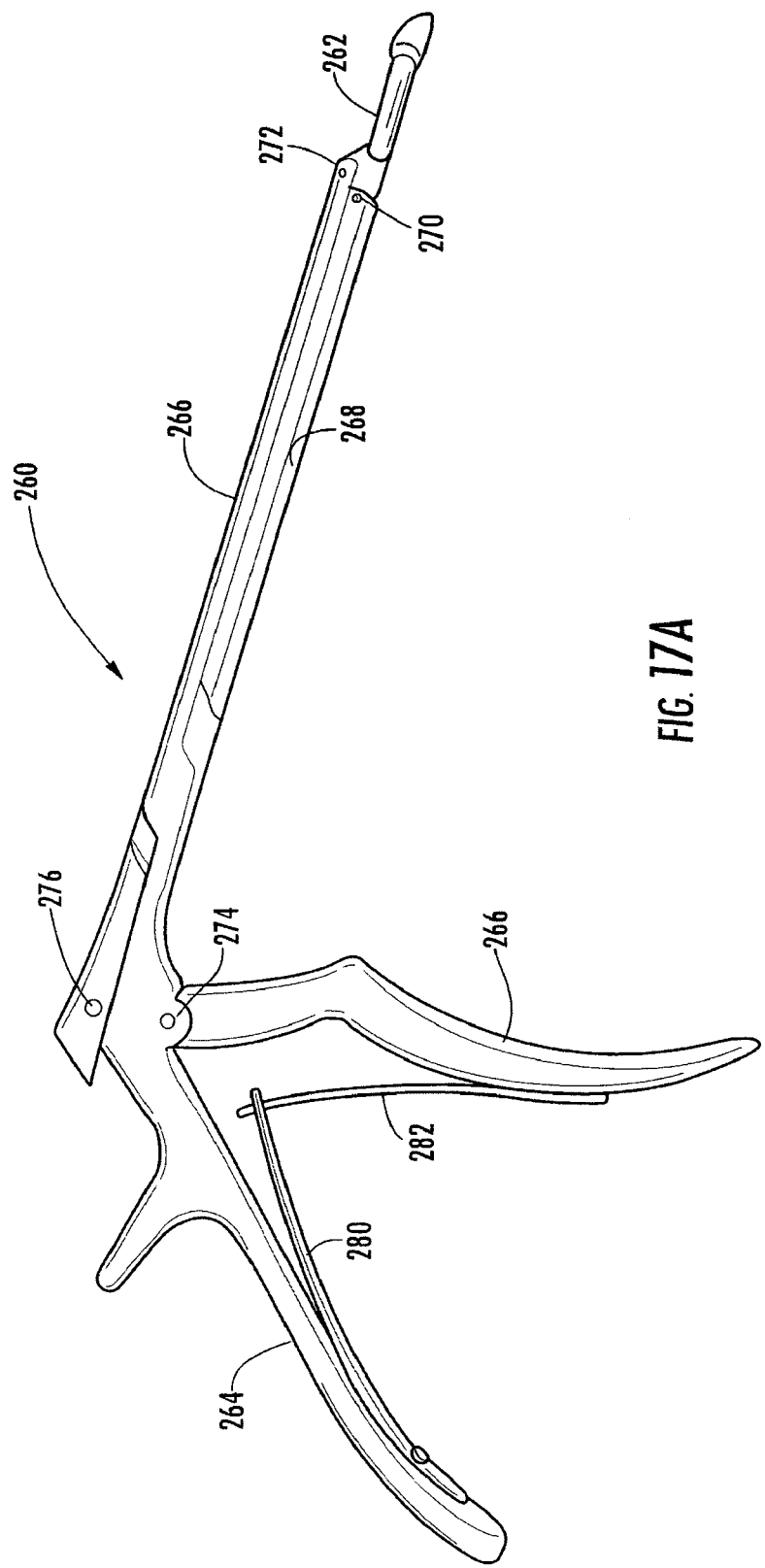
FIGS. 17A and 17B are perspective views of an alternative embodiment of a magnetic catcher.
Figure 17B:
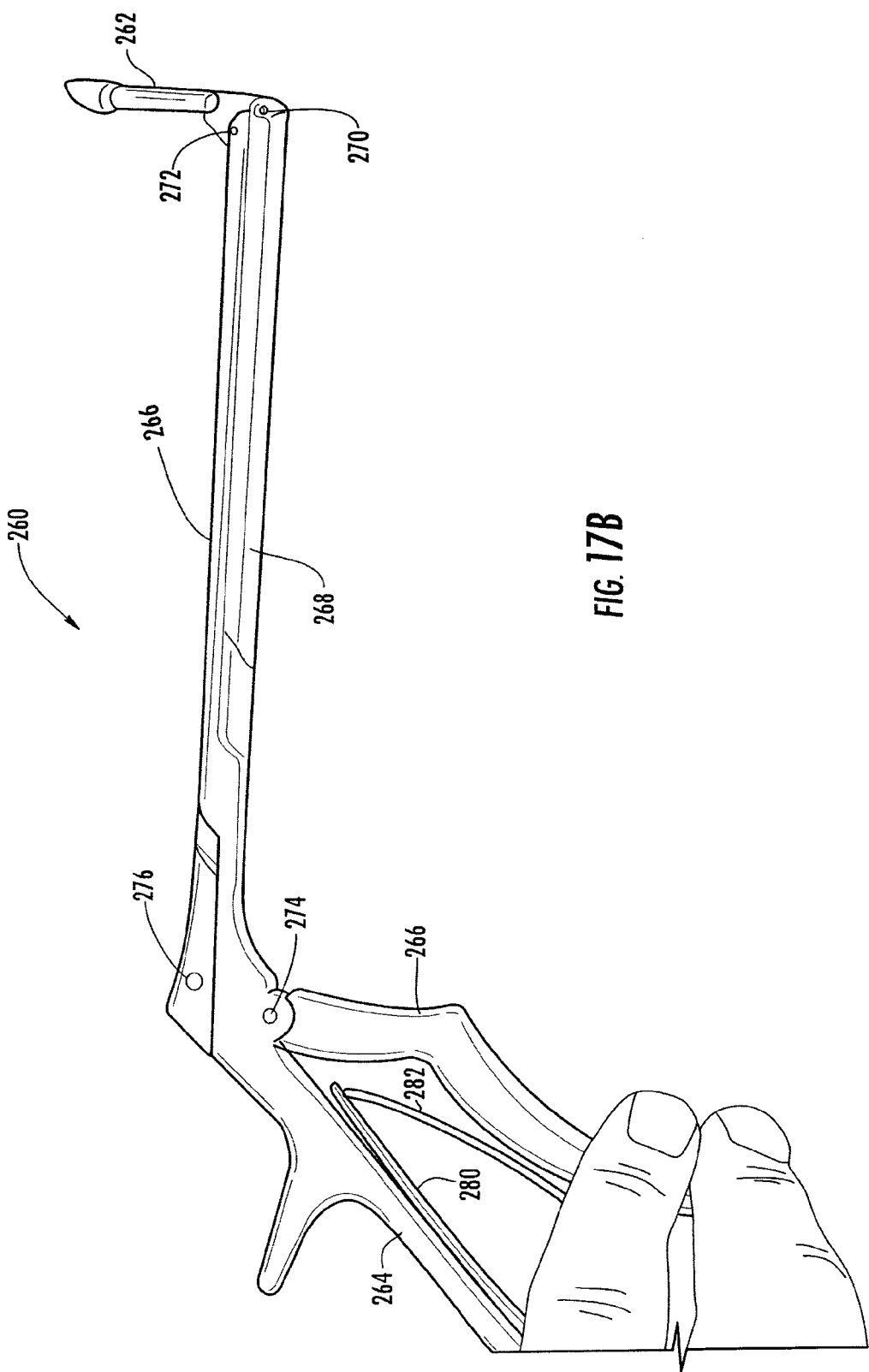

FIGS. 17A and 17B show an alternate embodiment to the magnetic device or wand 160 with a turnable magnetic catcher 162 located at the distal end of the wand 160, as shown in FIG. 10. In this embodiment the wand 260 includes a hand holding grip 264 and a trigger like component 266 pivotally attached thereto. Hand grip member 264 includes an elongated rod like member 266. An additional rod like member 268 is positioned adjacent elongated rod member 266 and is hingedly connected to trigger 266, via pivots 276 and 274 at one end, and hingedly connected to magnetic catcher 262, via pivot 272 at the opposite end. Magnetic catcher 262 is also pivotally connected to elongated rod member at pivot 270. Cantilevered flat springs 280 and 282 are positioned to bias the hand grip 264 and trigger 266 away from one another absent a force exerted by the operator's hand. In operation, the operator's fingers will grip trigger member 266 and pivotally move in towards the hand grip 264. When springs 280 and 282 abut the trigger and the hand grip they will act against the force exerted by the operator's fingers. The pivotal motion of trigger 266 relative to hand grip 264 will result in the relative axial displacement of rod like member 266 with respect to additional rod like member 268. The relative displacement will result in the pivotal movement of magnetic catcher 262, as shown in FIG. 17B, via the displacement of pivot 270 with respect to pivot 272. The magnetic wand 260 and magnetic catcher 262 are sized to fit with the internal cavity 114 of extender 112. The magnetic catcher 262 is constructed from any one of the magnetic materials noted above.

Figure 18A:
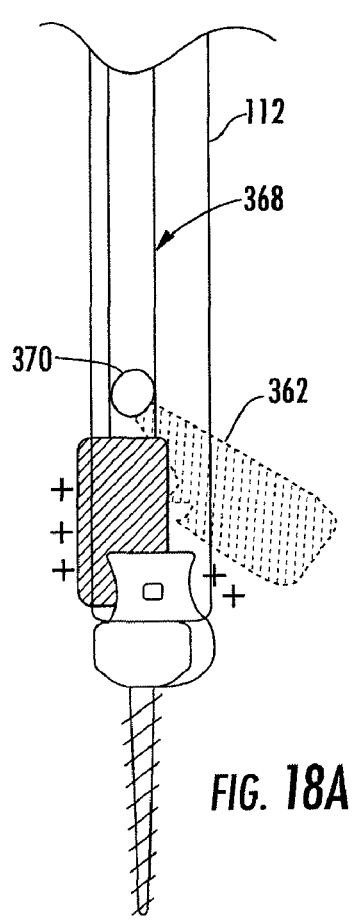
Figure 18E:
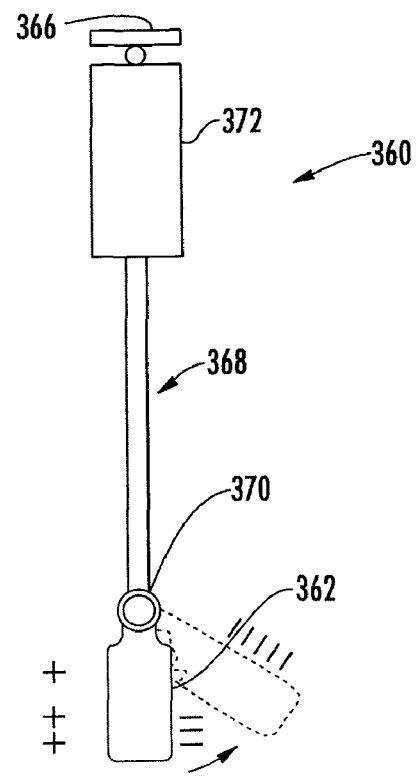
FIG. 18E is a perspective view of the catcher shown in FIGS. 18A-D removed from the extender.
Figure 18D:
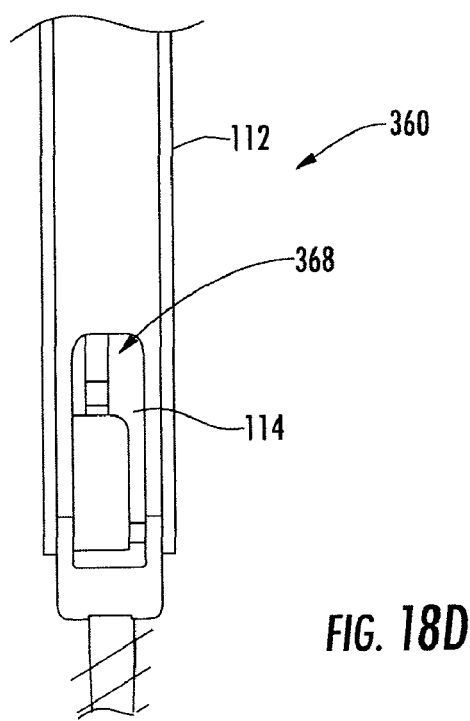
FIG. 18D is a front view of the catcher of shown in 18A-18C.

FIGS. 18A and 18E show another alternate embodiment to the magnetic device or wand 160 with a turnable magnetic catcher 162 located at the distal end of the wand 160, as shown in FIG. 10. In this embodiment the wand 360 includes a hand held rod 368 and a magnetic catcher 362. Wand 360 includes an upper cylindrical housing 372 and a push button actuator 366. Depression of push button actuator 366 causes pivotal motion of magnetic catcher 362 push that it may swing to a position external to cavity 114 to a point external of extender 112.

Figure 19B:
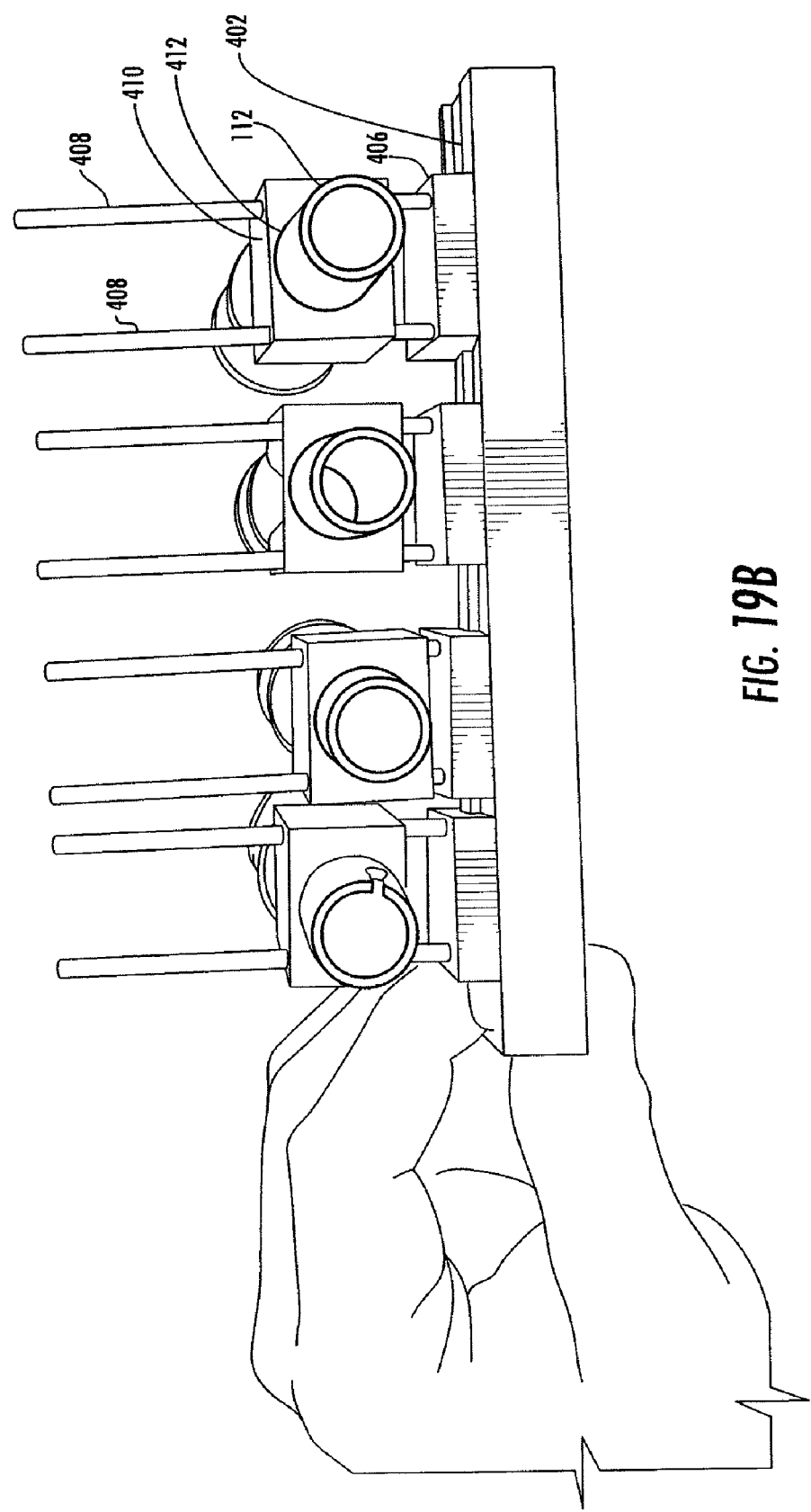
FIG. 19B is a top view of the installed device shown in FIG. 19A.
Figure 19C:
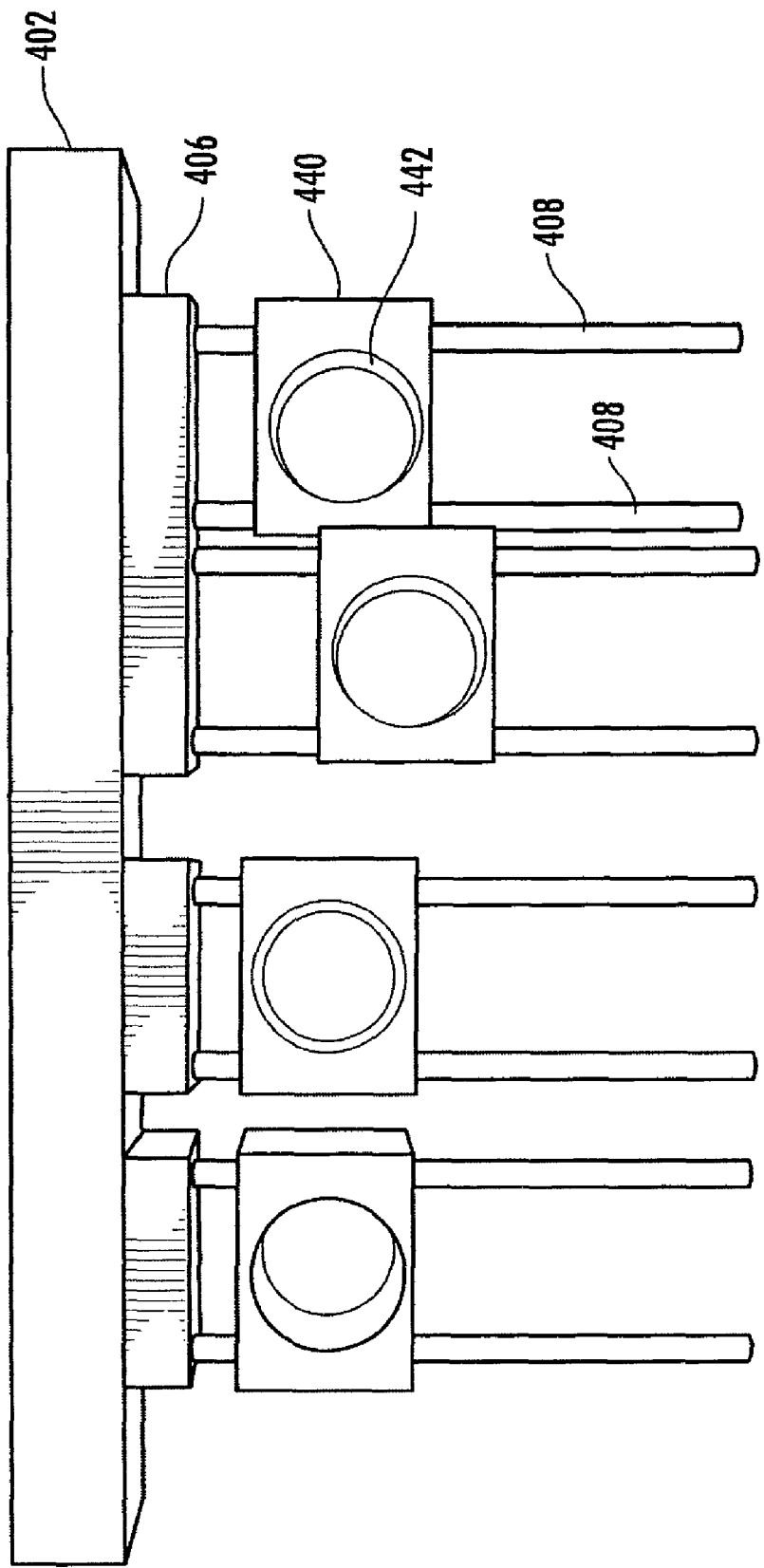
FIG. 19C is a top view of the device shown in FIG. 19A.
Figure 19D:
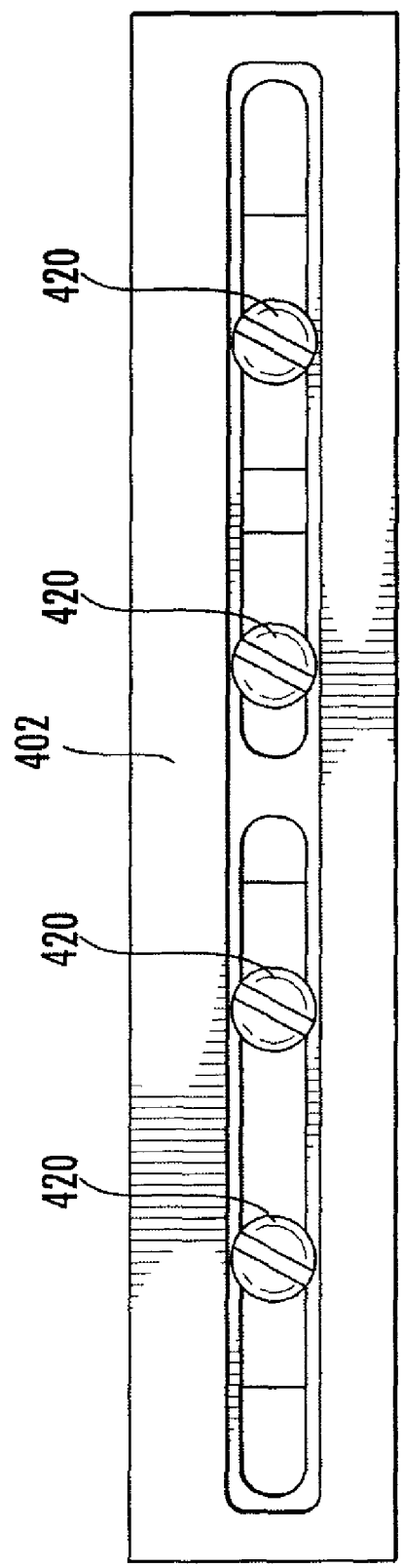
FIGS. 19D and 19E are opposite side views of the device shown in FIG. 19A.
Figure 19E:
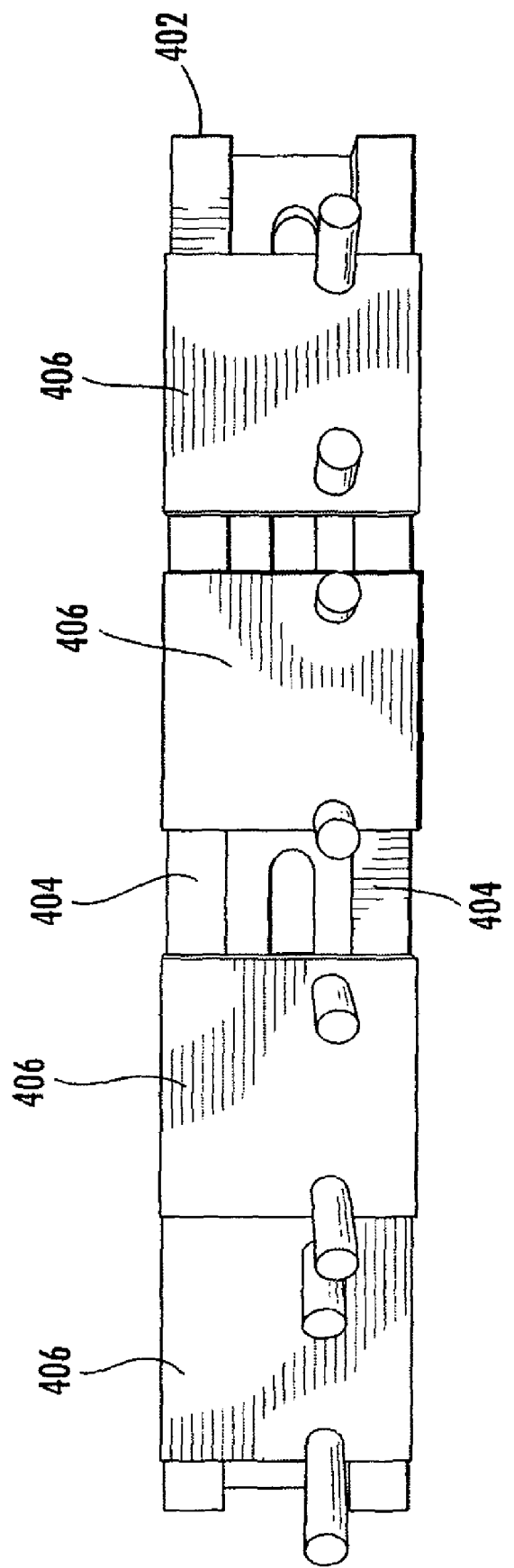

FIGS. 19A through 19E illustrate a device used to determine the curvature of rod 180 prior to insertion into the patient. The device provides a way to transfer the location of the extender passageways and associated pedicle screws to a position external of the body. This visualization permits the surgeon to provide the best configuration for rod 180 prior to insertion into the body. FIG. 19A shows a perspective side view of extenders 112A through 112D and the device 400 as it would be employed during a surgical procedure. The device 400 includes a plate 402 which includes a track 404 which extends along the length of the plate 402. Slidably mounted within track 402 are mounting blocks 406. The number of mounting blocks 406 used corresponds to the number of extender tubes 112 and associated pedicle screws. While four blocks 406 have been shown it should be understood that as few as two blocks and more than four blocks may be used. Each mounting block 406 carries a pair of support rods. Each pair of support rods 406 in turn are connected to an extender tube support block 410. Each extender tube support block 410 includes an aperture 412 sized to receive an extender tube 112. In use, each extender tube 112 is placed within a respective support block 410. The support block and mounting block associated with each extender tube is free to move along the track 404 within plate 402 such that tubes are properly aligned. Once each of the tubes are so positioned, a locking screw 420 is inserted in plate 402, through track 404 and into each mounting plate 406. When the extender tubes 112A-112D, as shown in FIG. 19A, are properly positioned and locked into place by screws 420 the surgeon can then proceed to shape the rod 180 in a manner presented by the upper surface of the extender tubes 112A-D as shown in FIG. 19A. The preforming of the rod 180 prior to insertion into the patient allows the surgeon to more easily thread the rod 180 through the extender passageways 132 located in extender tubes 112A-D that has been implanted within the patient and not visible to the surgeon.

Although the invention is described with reference to stabilization and fusion of adjacent spinal vertebrae, it is hereby contemplated that devices and methods disclosed herein could be used in all types of joints (ankle, interdigital, etc) found in the human or animal body. Although a rod-like member is exemplified herein, other such biocompatible devices known to one skilled in the art are also contemplated, for example, plates, clamps, etc.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A bone stabilization kit for facilitating navigation of a biocompatible device to a target area located in vivo, said kit comprising: a targeting member, said targeting member having a first end and a second end, said first end being constructed and arranged to penetrate and create a pathway through tissue, wherein said first end of said targeting member includes a magnetically influenced material, said second end constructed and arranged for attachment to a tether; a biocompatible device, said biocompatible device including a first end, a second end and an intermediate portion, said first end including a removable connection for removable attachment to a tether, said intermediate portion being constructed and arranged for attachment to said target area in vivo; a tether, said tether including a first end, a second end and an intermediate portion, said first end of said tether secured to said second end of said targeting member, said second end of said tether removable secured to said biocompatible device, said intermediate portion of said tether having a length sufficient to extend through said target area, said tether having sufficient tensile strength to pull said biocompatible device through said tissue pathway to said target area; at least one anchoring member for securing said intermediate portion of said biocompatible device to said target area; an extender having a first open end and second open end and an internal cavity therebetween, the first open end of said extender being removably attached to said at least one anchoring member, said second open end of said extender protruding a distance outside of a percutaneous exposure created in outer skin of a patient; and a wand sized to fit within the internal cavity of said extender, said wand including a magnetic catcher, said magnetic catcher constructed and arranged to cooperate with said magnetically influenced material of said targeting member for penetrating and creating said pathway through said tissue, wherein said magnetic catcher is pivotally connected to said wand, said wand including a mechanical linkage and a trigger member, said trigger member operable to cause said mechanical linkage to rotate said magnetic catcher with respect to said wand.

2. The bone stabilization kit of claim 1 wherein said intermediate portion of said tether includes a length sufficient to extend through said target area leaving said first end and said second end outside of said target area.

3. The bone stabilization kit of claim 1 wherein said tether is a single solid member.

4. The bone stabilization kit of claim 1 wherein said tether is a multi strand cable.

5. The bone stabilization kit of claim 1 wherein said tether is a cord.

6. The bone stabilization kit of claim 1 wherein said tether is cannulated.

7. The bone stabilization kit of claim 1 wherein said biocompatible device is a spinal implant.

* * * * *